United States Patent
Flax et al.

(10) Patent No.: US 9,861,308 B2
(45) Date of Patent: Jan. 9, 2018

(54) METHOD AND SYSTEM FOR MONITORING STRESS CONDITIONS

(71) Applicant: MEDIBIO LIMITED, Sydney, New South Wales (AU)

(72) Inventors: Matthew Flax, Leichhardt (AU); Aaron Wong, Warabrook (AU); Michael Player, Randwick (AU); Todd Jolly, Merewether (AU); Hans Stampfer, Mount Lawley (AU)

(73) Assignee: MEDIBIO LIMITED, Sydney (AU)

( * ) Notice: Subject to any disclaimer, the term of this patent is extended or adjusted under 35 U.S.C. 154(b) by 0 days.

(21) Appl. No.: 15/403,549

(22) Filed: Jan. 11, 2017

(65) Prior Publication Data

US 2017/0156657 A1     Jun. 8, 2017

Related U.S. Application Data

(63) Continuation of application No. PCT/AU2016/050491, filed on Jun. 15, 2016.
(Continued)

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0022* (2013.01); *A61B 5/02405* (2013.01);
(Continued)

(58) Field of Classification Search
CPC ... A61B 5/165; A61B 5/0022; A61B 5/02405; A61B 5/02438; A61B 5/1118;
(Continued)

(56) References Cited

U.S. PATENT DOCUMENTS

| 4,832,038 A | 5/1989 | Arai et al. |
| 6,245,021 B1 | 6/2001 | Stampfer |

(Continued)

FOREIGN PATENT DOCUMENTS

| JP | 2007-7149 A | 1/2007 |
| WO | WO 98-46128 A1 | 10/1998 |

OTHER PUBLICATIONS

Iverson et al., "Reliability of circadian heart pattern analysis in psychiatry," Psychiatric Quarterly, vol. 73, No. 3, Fall 2002, pp. 195-203.
(Continued)

*Primary Examiner* — Catherine Voorhees
(74) *Attorney, Agent, or Firm* — Birch, Stewart, Kolasch & Birch, LLP

(57) ABSTRACT

A computer-implemented method of assessing a stress condition of a subject (106) includes receiving (302), as input, a heartbeat record (200) of the subject. The heartbeat record comprises a sequence of heartbeat data samples obtained over a time span which includes a pre-sleep period (208), a sleep period (209) having a sleep onset time (224) and a sleep conclusion time (226), and a post-sleep period (210). At least the sleep onset time and the sleep conclusion time are identified (304) within the heartbeat record. A knowledge base (124) is then accessed (306), which comprises data obtained via expert evaluation of a training set of subjects and which embodies a computational model of a relationship between stress condition and heart rate characteristics. Using information in the knowledge base, the computational model is applied (308) to compute at least one metric associated with the stress condition of the subject, and to generate an indication of stress condition based upon the metric. The indication of stress condition is provided (310) as output.

18 Claims, 13 Drawing Sheets

Related U.S. Application Data

(60) Provisional application No. 62/175,826, filed on Jun. 15, 2015.

(51) Int. Cl.
   *A61B 5/024* (2006.01)
   *A61B 5/11* (2006.01)
   *G06F 19/00* (2011.01)
   *H04B 1/38* (2015.01)
   *H04B 1/3827* (2015.01)

(52) U.S. Cl.
   CPC ........ *A61B 5/02438* (2013.01); *A61B 5/1118* (2013.01); *A61B 5/4809* (2013.01); *A61B 5/4815* (2013.01); *A61B 5/7246* (2013.01); *A61B 5/7267* (2013.01); *A61B 5/7278* (2013.01); *G06F 19/323* (2013.01); *G06F 19/3418* (2013.01); *H04B 1/3827* (2013.01); *A61B 2562/0219* (2013.01)

(58) Field of Classification Search
   CPC ... A61B 5/4809; A61B 5/4815; A61B 5/7246; A61B 5/7267; A61B 5/7278; A61B 2562/0219; G06F 19/323; G06F 19/3418; H04B 1/3827
   See application file for complete search history.

(56) References Cited

U.S. PATENT DOCUMENTS

| | | |
|---|---|---|
| 6,942,622 B1 | 9/2005 | Turcott |
| 7,640,055 B2 | 12/2009 | Geva et al. |
| 7,689,437 B1 | 3/2010 | Teller et al. |
| 8,306,610 B2 | 11/2012 | Mirow |
| 8,369,936 B2 | 2/2013 | Farringdon et al. |
| 8,452,387 B2 | 5/2013 | Osorio et al. |
| 8,568,330 B2 | 10/2013 | Mollicone et al. |
| 8,679,009 B2 | 3/2014 | Osorio |
| 8,744,562 B2 | 6/2014 | Giftakis et al. |
| 9,075,910 B2 | 7/2015 | Bhavaraju et al. |
| 9,396,486 B2 | 7/2016 | Stivoric et al. |
| 2002/0002327 A1 | 1/2002 | Grant et al. |
| 2004/0111033 A1 | 6/2004 | Oung et al. |
| 2004/0236236 A1 | 11/2004 | Yanagidaira et al. |
| 2005/0148897 A1 | 7/2005 | Cho et al. |
| 2005/0245790 A1 | 11/2005 | Bergfalk et al. |
| 2008/0033304 A1 | 2/2008 | Dalal et al. |
| 2008/0167565 A1 | 7/2008 | Laitio et al. |
| 2009/0149778 A1 | 6/2009 | Naujokat et al. |
| 2009/0157662 A1 | 6/2009 | Suffin et al. |
| 2009/0192399 A1 | 7/2009 | Choi et al. |
| 2010/0069762 A1 | 3/2010 | Mietus et al. |
| 2010/0113893 A1 | 5/2010 | Cohen et al. |
| 2010/0217099 A1 | 8/2010 | LeBoeuf et al. |
| 2011/0112442 A1 | 5/2011 | Meger et al. |
| 2011/0184298 A1 | 7/2011 | De Marchena et al. |
| 2012/0232414 A1* | 9/2012 | Mollicone .............. A61B 5/024 600/508 |
| 2013/0079602 A1 | 3/2013 | Picard et al. |
| 2013/0245396 A1 | 9/2013 | Berman et al. |
| 2013/0262155 A1 | 10/2013 | Hinkamp |
| 2013/0296730 A1 | 11/2013 | Osorio et al. |
| 2014/0031651 A1 | 1/2014 | Chon |
| 2014/0046144 A1 | 2/2014 | Jayaraman et al. |
| 2014/0058279 A1 | 2/2014 | Shinba |
| 2014/0081090 A1 | 3/2014 | Picard et al. |
| 2014/0088378 A1 | 3/2014 | Muzet |
| 2014/0115008 A1 | 4/2014 | Stivoric et al. |
| 2014/0122496 A1 | 5/2014 | Stivoric et al. |
| 2014/0122537 A1 | 5/2014 | Stivoric et al. |
| 2014/0136450 A1 | 5/2014 | Lee |
| 2014/0180020 A1 | 6/2014 | Stivoric et al. |
| 2014/0180022 A1 | 6/2014 | Stivoric et al. |
| 2014/0180598 A1 | 6/2014 | Stivoric et al. |
| 2014/0200414 A1 | 7/2014 | Osorio |
| 2014/0206945 A1 | 7/2014 | Liao |
| 2014/0206946 A1 | 7/2014 | Kim et al. |
| 2014/0213854 A1 | 7/2014 | Stivoric et al. |
| 2014/0213856 A1 | 7/2014 | Teller et al. |
| 2014/0213857 A1 | 7/2014 | Teller et al. |
| 2014/0213938 A1 | 7/2014 | Stivoric et al. |
| 2014/0214836 A1 | 7/2014 | Stivoric et al. |
| 2014/0220525 A1 | 8/2014 | Stivoric et al. |
| 2014/0221730 A1 | 8/2014 | Stivoric et al. |
| 2014/0221773 A1 | 8/2014 | Stivoric et al. |
| 2014/0221774 A1 | 8/2014 | Teller et al. |
| 2014/0221775 A1 | 8/2014 | Stivoric et al. |
| 2014/0221776 A1 | 8/2014 | Stivoric et al. |
| 2014/0221780 A1 | 8/2014 | Goldberger et al. |
| 2014/0221789 A1 | 8/2014 | Pacione et al. |
| 2014/0221790 A1 | 8/2014 | Pacione et al. |
| 2014/0221791 A1 | 8/2014 | Pacione et al. |
| 2014/0221849 A1 | 8/2014 | Farringdon et al. |
| 2014/0221850 A1 | 8/2014 | Farringdon et al. |
| 2014/0222732 A1 | 8/2014 | Stivoric et al. |
| 2014/0222733 A1 | 8/2014 | Stivoric et al. |
| 2014/0222734 A1 | 8/2014 | Stivoric et al. |
| 2014/0222735 A1 | 8/2014 | Stivoric et al. |
| 2014/0222847 A1 | 8/2014 | Stivoric et al. |
| 2014/0240124 A1* | 8/2014 | Bychkov .............. A61B 5/0026 340/539.12 |
| 2014/0275854 A1* | 9/2014 | Venkatraman ......... A61B 5/721 600/301 |
| 2014/0308636 A1 | 10/2014 | Stivoric et al. |
| 2014/0308639 A1 | 10/2014 | Stivoric et al. |
| 2014/0309939 A1 | 10/2014 | Stivoric et al. |
| 2014/0309940 A1 | 10/2014 | Stivoric et al. |
| 2014/0310105 A1 | 10/2014 | Stivoric et al. |
| 2014/0310294 A1 | 10/2014 | Stivoric et al. |
| 2014/0310298 A1 | 10/2014 | Stivoric et al. |
| 2014/0316230 A1 | 10/2014 | Denison et al. |
| 2014/0316885 A1 | 10/2014 | Stivoric et al. |
| 2014/0317039 A1 | 10/2014 | Stivoric et al. |
| 2014/0317042 A1 | 10/2014 | Stivoric et al. |
| 2014/0317119 A1 | 10/2014 | Stivoric et al. |
| 2014/0317135 A1 | 10/2014 | Stivoric et al. |
| 2014/0342328 A1 | 11/2014 | Pacione et al. |
| 2014/0344282 A1 | 11/2014 | Stivoric et al. |
| 2015/0025403 A1 | 1/2015 | Chang et al. |
| 2015/0099987 A1* | 4/2015 | Bhatkar ................ A61B 5/165 600/479 |
| 2015/0126890 A1 | 5/2015 | Scheib |
| 2015/0126891 A1 | 5/2015 | Scheib |
| 2015/0142553 A1 | 5/2015 | Kodra et al. |
| 2015/0148621 A1 | 5/2015 | Sier |
| 2015/0150516 A1 | 6/2015 | Tochikubo et al. |
| 2015/0182129 A1 | 7/2015 | Colley et al. |
| 2015/0208986 A1 | 7/2015 | Gottesman |
| 2015/0282722 A1 | 10/2015 | Klepp |
| 2015/0289809 A1 | 10/2015 | Pacione et al. |
| 2015/0289810 A1 | 10/2015 | Pacione et al. |
| 2015/0374301 A1 | 12/2015 | Teller et al. |
| 2016/0015318 A1 | 1/2016 | Bhavaraju et al. |
| 2016/0113567 A1 | 4/2016 | Osvath et al. |
| 2016/0310022 A1 | 10/2016 | Stivoric et al. |
| 2016/0317073 A1 | 11/2016 | Brockway et al. |
| 2016/0338640 A1 | 11/2016 | Chan et al. |
| 2016/0338641 A1 | 11/2016 | Chan et al. |
| 2016/0375245 A1 | 12/2016 | Frei et al. |
| 2016/0379505 A1 | 12/2016 | el Kaliouby et al. |
| 2017/0071546 A1 | 3/2017 | Jain et al. |
| 2017/0127993 A1 | 5/2017 | Olivier et al. |

OTHER PUBLICATIONS

Medibio: ASX Announcements, Accessed Mar. 16, 2017, 12 pages, <http://Medibio.Com.Au/Asx-Announcements/>.

Stampfer et al., "Variations in circadian heart rate in psychiatric disorders: theoretical and practical implications," Dovepress, ChronoPhysiology and Therapy, vol. 3, Apr. 18, 2013, pp. 41-50.

(56) References Cited

OTHER PUBLICATIONS

Stampfer, "The Relationship between Psychiatric Illness and the Circadian Pattern of Heart Rate," Aust Nz J Psychiatry, vol. 32, Issue 2, 1998, pp. 187-198 (13 pages).

Written Opinion of the International Searching Authority and International Search Report (Forms PCT/ISA/237 and PCT/ISA/210), dated Sep. 12, 2016, for International Application No. PCT/AU2016/050491.

Written Opinion of the International Searching Authority and International Search Report (Forms PCT/ISA/237 and PCT/ISA/210), dated Sep. 21, 2016, for International Application No. PCT/AU2016/050490.

\* cited by examiner

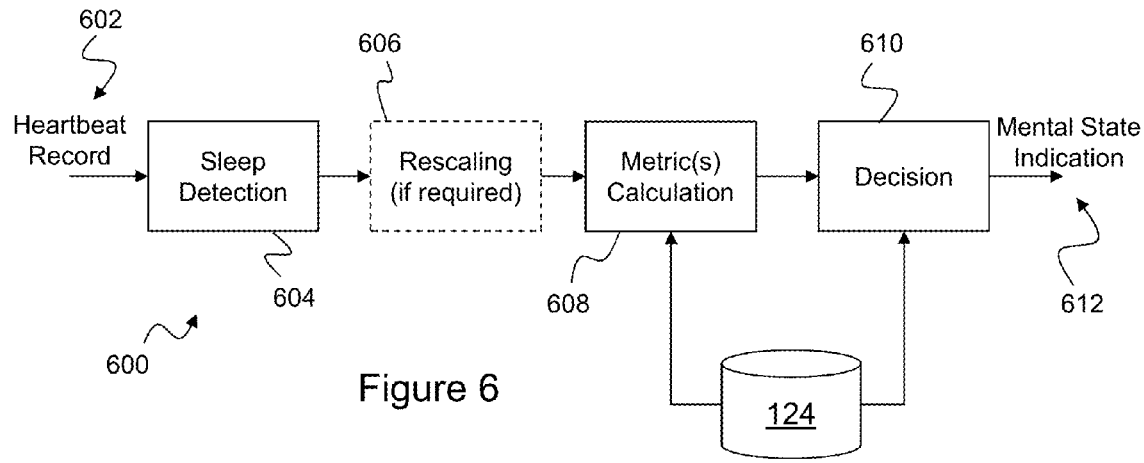
Figure 6
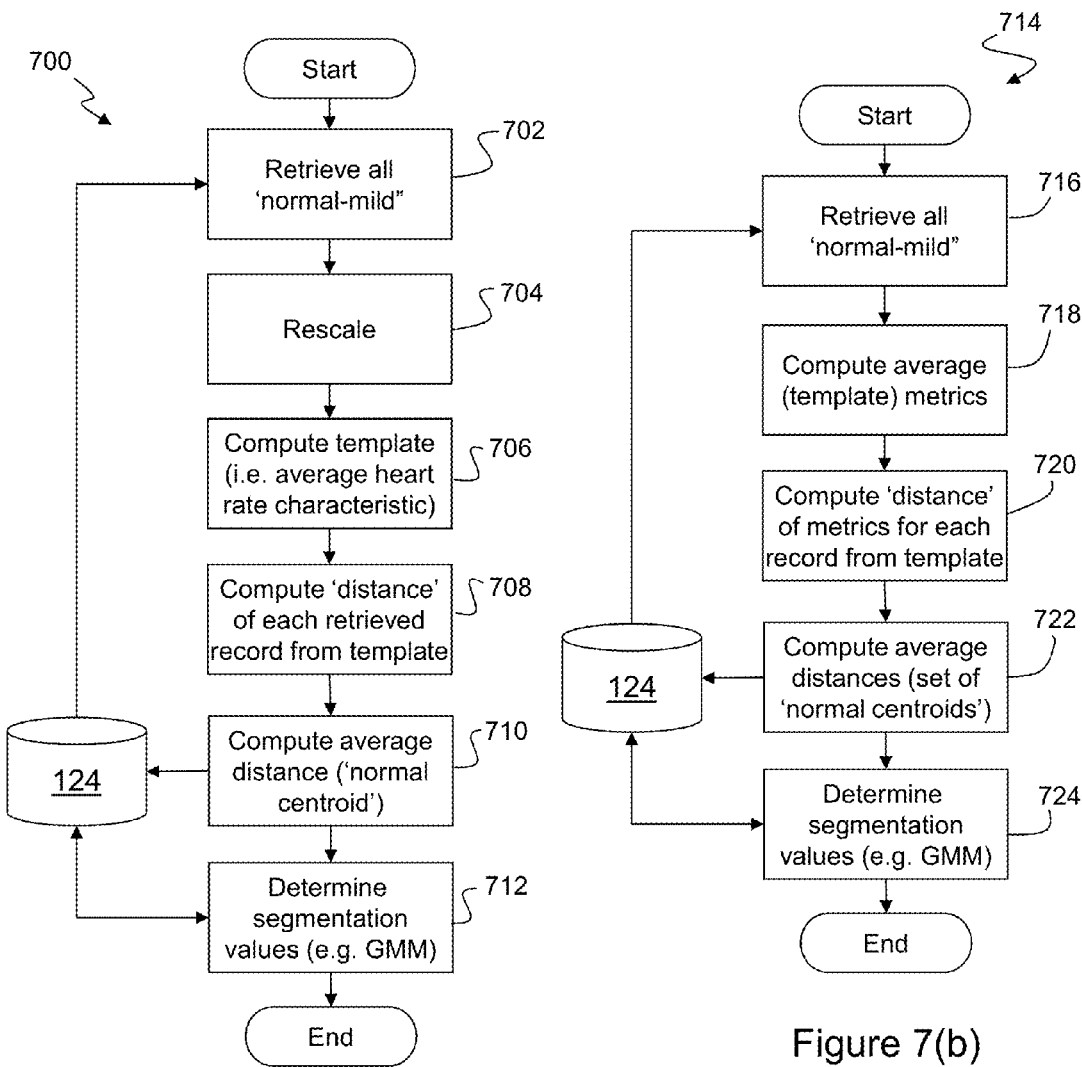
Figure 7(a)
Figure 7(b)

METHOD AND SYSTEM FOR MONITORING STRESS CONDITIONS

CROSS REFERENCE TO RELATED APPLICATIONS:

This application is a Continuation of PCT International Application No. PCT/AU2016/050491, filed on Jun. 15, 2016, which claims priority under 35 U.S.C. 119(e) to U.S. Provisional Application No. 62/175,826, filed on Jun.15, 2015, all of which are hereby expressly incorporated by reference into the present application.

FIELD OF THE INVENTION

The present invention relates generally to the field of mental health care, and more particularly to methods and systems, along with associated hardware and software components, for monitoring stress levels based upon measurements of heart rate.

BACKGROUND TO THE INVENTION

Stress is a natural human response to pressure when faced with threatening or challenging situations. A certain level of stress is normal, and can be beneficial in enabling people to achieve peak performance. The human body should revert back to its normal state after a certain period of time, following a stress-inducing experience. However, this reversion to normal can be suppressed when individuals are subjected to frequent or repetitive stressful situations. Long-lasting or overwhelming stress can have a negative impact upon human health, wellbeing, relationships, work and general enjoyment of life.

Extended or heightened levels of stress are associated with anxiety, depression, psychosomatic illness, suppressed immunity, general losses of energy and productivity, and other associated health problems. In the workplace, this results in increases in absenteeism and presenteeism. Safe Work Australia estimated the cost of work-related stress during 2008 and 2009 at around A$5.3 billion annually. US studies of the economic impact of stress, at around the turn of the century, variously estimated costs of between US$200 to US$300 billion annually.

Trained health care professionals are able to identify typical symptoms of stress-related problems. However, the signs of excessive stress are often undetected by the affected individual until the psychological and physical health impacts have become significant. Furthermore, although employers, health insurers, and society more broadly could achieve significant economic and social benefits from early detection and management of stress, the tools available to enable personal or corporate management and monitoring of stress levels, other than through regular appointments with trained health care professionals, are extremely limited.

Self-assessment methods, typically based upon questionnaires, have been developed to assist individuals in monitoring and managing their mental health. For example, the Social Readjustment Rating Scale (SRRS), originally developed in 1967 by Holmes and Rahe, comprises a list of 43 stressful life events that can contribute to adverse health outcomes. However, the Holmes and Rahe Stress Scale identifies only the individual's exposure to stress based upon the experience of recent major life events. Questionnaires directed to assessment of a current mood state of an individual, such as the Depression Anxiety Stress Scale (DASS), developed at the University of New South Wales, are based upon a subjective assessment of mood, and are better suited to distinguishing between different mental health conditions, but are not able to monitor, on a day-to-day basis, differences between stress levels that have not yet progressed significantly towards more serious conditions.

Accordingly, it would be desirable to develop new methods and systems for monitoring and managing stress levels that can be self-administered by an individual, supported in the workplace, are objective, and are able to differentiate between different levels of stress, to enable early identification of emerging problems.

The present invention has been devised in order to address these requirements.

SUMMARY OF THE INVENTION

In one aspect, the present invention provides a computer-implemented method of assessing a mental state of a subject, the method comprising:

receiving, as input, a heartbeat record of the subject, which comprises a sequence of heartbeat data samples obtained over a time span which includes a pre-sleep period, a sleep period having a sleep onset time and a sleep conclusion time, and a post-sleep period;

identifying, within the heartbeat record, at least the sleep onset time and the sleep conclusion time;

accessing a knowledge base comprising data obtained via expert evaluation of a training set of subjects and embodying a computational model of a relationship between mental state and heart rate characteristics;

using information in the knowledge base, applying the computational model to compute at least one metric associated with the mental state of the subject, and to generate an indication of mental state based upon the metric; and providing, as output, the indication of mental state.

Embodiments of the invention may comprise expert systems in which the knowledge base contains information generated via machine-learning methodologies. For example, the knowledge base may embody measured heart rate data for a plurality of subjects comprising the training set, along with the results of expert assessment of each subject in the training set. In such embodiments, the knowledge base captures salient information regarding the relationship between the mental state of each subject in the training set, and measured heart rate characteristics, in a form such that a corresponding computational model may be employed to predict the expert assessment of subsequent unseen test subjects.

According to embodiments of the invention, the indication of mental state comprises an indication of stress levels experienced by the subject. For example, the indication of mental state may distinguish between three levels of stress, such as a normal-to-mild stress level, a moderate stress level, and a severe stress level.

Identifying the sleep onset and conclusion times may involve the use of auxiliary input data. In some embodiments, for example, the input heartbeat record may be accompanied by a record of activity of the subject measured using an activity monitor, such as an accelerometer.

In some embodiments, the knowledge base may comprise a template heart rate characteristic which may be obtained, for example, by averaging scaled and normalised heart rate characteristics of subjects in the training set who have been assessed by an expert assessor as experiencing normal or low levels of stress. The knowledge base may further comprise a normal centroid value, comprising a measure of an average distance of the heartbeat characteristics of subjects in the training set assessed as normal from the template characteristic. The knowledge base may further comprise a set of segmentation points, representing variations in distance from the template characteristic, relative to the normal centroid and, defining classification boundaries between different indications of mental state. For example, two segmentation values may be provided to distinguish between three different levels of stress.

In alternative embodiments, heart rate characteristics of subjects may be processed to compute a plurality of associated metrics. In some examples, four metrics are employed: a mean-awake heart rate; a ratio between mean-awake and -asleep heart rates; a slope of heart rate during the first half of the sleep period; and a slope of heart rate in the second half of the sleep period. As will be appreciated, these particular four metrics can be computed by fitting a piecewise linear heart rate characteristic model to the received heartbeat record of a subject.

A knowledge base employing a plurality of metrics may contain an array of values of the metrics corresponding with a template characteristic based upon subjects assessed by an expert as having normal or low stress levels, as described above. The knowledge base may further contain an array of normal centroid values, corresponding with each one of the plurality of metrics, and computed by averaging the magnitudes of the differences between the respective metrics for all subjects assessed by the expert as having normal or low stress levels, and the equivalent template characteristic metrics. A comparison between the computed metrics for the received heartbeat record of the subject, and the corresponding normal centroid values, may be used to compute a measure of distance of the subject's mental state from a 'normal' mental state. The knowledge base may further contain an array of segmentation values defining distance measures corresponding with boundaries between mental state classifications.

In still further embodiments, a mental state classification based upon a k nearest neighbour (k-NN) computational model is employed. In such embodiments, the knowledge base may contain an array of (M+1) dimensional vectors, where M is the number of the plurality of metrics employed, in which each vector corresponds with a subject in the training set, and comprises values for each of the computed metrics, and a value of the corresponding expert assessment of the subject. The knowledge base may also contain an optimised value of the number of nearest-neighbours parameter K.

In the k-NN computational model, an assessment of the mental state of the subject is performed by computing the plurality of metrics based upon the received heartbeat record, and determining its K nearest neighbours from the training set, within the M dimensional space defined by the plurality of metrics. The expert assessments associated with the K nearest neighbours are then used to generate an indication of the mental state of the subject. In some embodiments, a 'voting' system is employed, in which the indication of mental state of the subject is generated as the most-frequently occurring mental state associated with the identified K nearest neighbours from the training set.

In another aspect, the invention provides a computer-implemented system for assessing a mental state of a subject, the system comprising:

at least one microprocessor;

at least one non-volatile storage device containing a knowledge base comprising data obtained via expert evaluation of a training set of subjects and embodying a computational model of a relationship between mental state and heart rate characteristics;

at least one computer-readable memory device operatively associated with the microprocessor; and an input/output interface operatively associated with the microprocessor, wherein the memory device contains computer-executable instruction code which, when executed via the microprocessor, causes the microprocessor to effect a method comprising steps of:

receiving, via the input/output interface, a heartbeat record of the subject, which comprises a sequence of heartbeat data samples obtained over a timespan which includes a pre-sleep period, a sleep period having a sleep onset time and a sleep conclusion time, and a post-sleep period;

identifying, within the heartbeat record, at least the sleep onset time and the sleep conclusion time;

using information in the knowledge base, applying the computational model to compute at least one metric associated with the mental state of the subject, and to generate an indication of mental state based upon the metric; and providing, via the input/output interface, the indication of the mental state of the subject.

The input/output interface may be a network interface providing access to a wide area network, such as the Internet.

In some embodiments of the invention, the heartbeat record of the subject may be obtained via a heart rate monitor device worn by the subject during the timespan including the pre-sleep period, the sleep period and the post-sleep period. The heartbeat monitor may comprise a wireless interface, such as a Bluetooth interface, for communication with a network-connected device, such as a smartphone, a tablet computer, a notebook computer, or a desktop computer. Alternatively, or additionally, the heart rate monitor device may comprise a wired interface, such as a USB interface, for connection to a network-connected device.

An application may be provided for execution on the network-connected device to assist the subject in performing a measurement of a heartbeat record. Assistance may include providing the subject with instructions for fitting the heart rate monitor device, as well as for transferring measured heart rate data from the heart rate monitor device to the network-connected device.

The heartbeat record of the subject may be transferred from the network-connected device to the mental state assessment system via the wide area network, e.g. the Internet.

Further features and benefits of the invention will be apparent from the following description of embodiments, which is provided by way of example only and should not be taken to limit the scope of the invention as it is defined in any of the preceding statements, or in the claims appended hereto.

BRIEF DESCRIPTION OF THE DRAWINGS

Embodiments of the invention will now be described with reference to the accompanying drawings in which like reference numerals indicate like features, and wherein:

FIG. 6 is a block diagram illustrating the main software processing components of a computer implementation of embodiments of the invention;

FIGS. 7(a) to 7(c) are flowcharts of knowledge base construction methods corresponding with the computational models of FIGS. 4(a) to 4(c), while

DETAILED DESCRIPTION OF EMBODIMENTS

Figure 1:
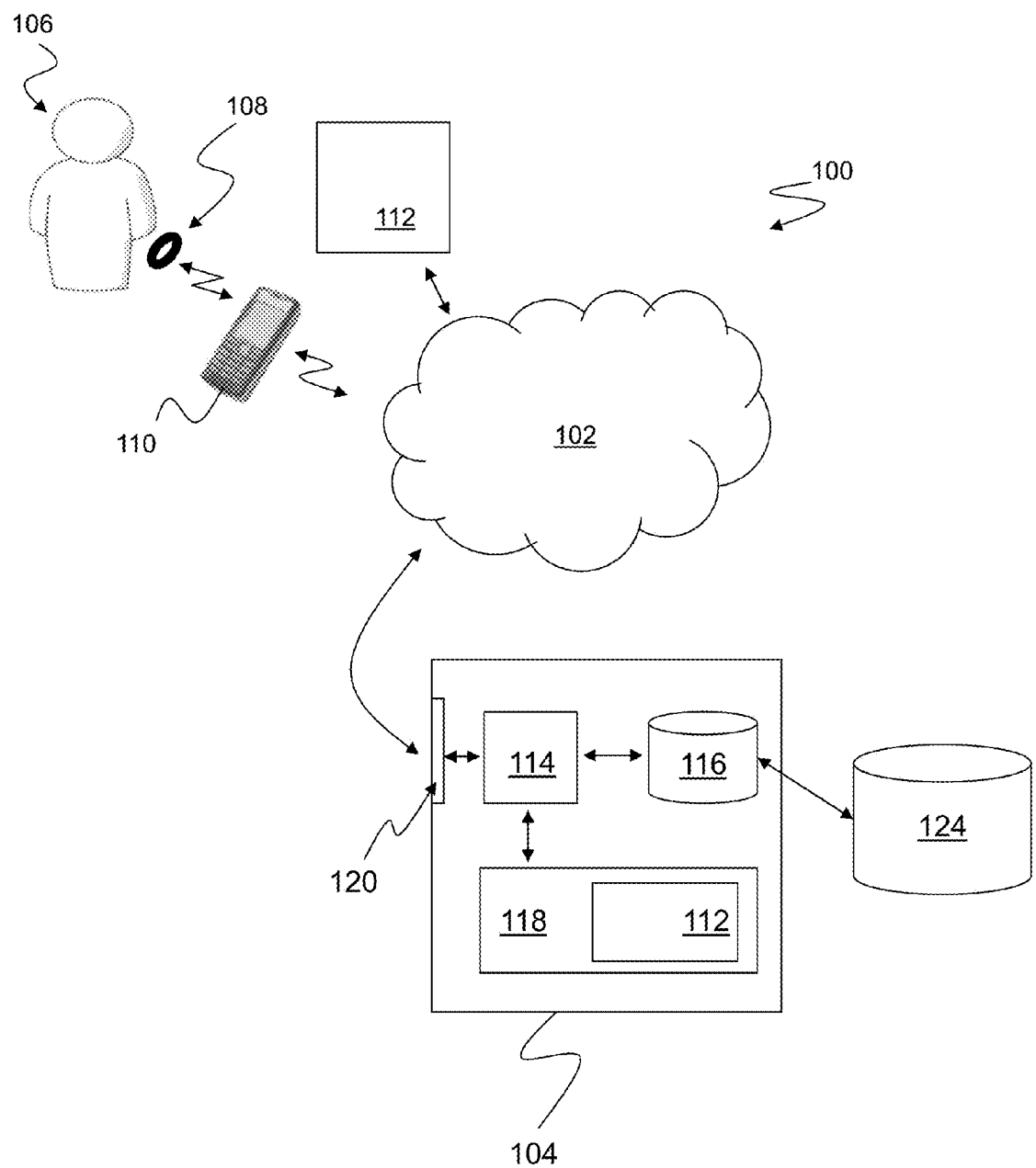
FIG. 1 is a schematic diagram illustrating a system for assessing mental state of a subject, embodying the invention.

FIG. 1 is a block diagram illustrating an online system 100 embodying the invention. The system 100 employs a wide area communications network 102, typically being the Internet, for messaging between different components of the system, each of which generally comprises one or more computing devices.

The system 100 includes an assessment server 104 and a remotely located assessment subject 106. The subject 106 is provided with a heart rate monitor 108, which is capable of communications with one or more portable devices, such as smartphone 110, and/or one or more desktop devices such as a personal computer 112. Communications between the heart rate monitor 108 and smartphone 110 are preferably via a wireless communications channel, such as Bluetooth. Other types of communications channel suitable for transfer of data between the heart rate monitor 108 and devices 110, 112 include Wi-Fi, wired Ethernet, and other forms of wired connections, such as USB.

In some embodiments, such as those described herein, heart rate data collected by the heart rate monitor 108 is transferred to another user device, such as smartphone 110 or desktop PC 112, and then transferred to the assessment server 104. However, in other embodiments of the invention a smart heart rate monitor 108 may include a network interface, such as a Wi-Fi interface, enabling it to connect and transfer data directly to the assessment server 104 via the Internet 102. In still further embodiments, the functionality of the assessment server 104 may be provided at the location of the assessment subject 106, such as via software made available for installation on the subject PC 112. It should therefore be appreciated that the online architecture of the system 100, while presently considered advantageous, is not the only way in which the invention may be implemented.

Turning now to the assessment server 104, it may generally comprise one or more computers, each of which includes at least one microprocessor 114. The number of computers and processors 114 will generally depend upon the required processing capacity of the system, which in turn depends upon the anticipated workload, i.e. the number of assessment subjects 106 having access to the server 104, and the volumes of data to be processed. In some embodiments, a third-party cloud-computing platform may be employed for the server 104, thereby enabling the physical hardware resources to be allocated, and changed, dynamically in response to demand. However, for simplicity in the remainder of the description, it is assumed that the exemplary assessment server 104 includes a single computer with a single microprocessor 114.

The microprocessor 114 is interfaced to, or otherwise operably associated with, a non-volatile memory/storage device 116. The non-volatile storage 116 may be a hard disk drive, and/or may include a solid-state non-volatile memory, such as read only memory (ROM), flash memory, or the like. The microprocessor 114 is also interfaced to volatile storage 118, such as random access memory (RAM) which contains program instructions and transient data relating to the operation of the server 104. In a conventional configuration, the storage device 116 may contain operating system programs and data, as well as other executable application software necessary to the intended functions of the assessment server 104. In the embodiments shown, the storage device 116 also contains program instructions which, when executed by the processor 114, enable the assessment server 104 to perform operations relating to the implementation of a mental state assessment method, and more particularly a method of assessing stress levels of the subject 106, embodying the invention. In operation, instructions and data held on the storage device 116 are transferred to volatile memory 118 for execution on demand.

The microprocessor 114 is also operably associated with a network interface 120 in a conventional manner. The network interface 120 facilitates access to one or more data communications networks, such as the Internet 102, employed for communication between the server 104 and subject devices, e.g. 110, 112.

In use, the volatile storage 118 includes a corresponding body 122 of program instructions configured to perform processing and operations embodying features of the present invention, comprising various steps in the processes described below with reference to the flowcharts, data structures, and software architectures illustrated in FIGS. 3 to 7.

Furthermore, in the presently described embodiment, the program instructions 122 include instructions implementing communications with one or more client applications, such as an application executing on the subject smartphone 110. These communications operations enable heartbeat records of the subject 106, recorded using the heart rate monitor 108, to be received for processing by the assessment server 104.

The program instructions 122 may further include instructions embodying a web server application. Data stored in the non-volatile 116 and volatile 118 storage may then include web-based code for presentation and/or execution on subject devices (e.g. HTML or JavaScript) facilitating a web-based interface to the assessment server. The web-based interface may, for example, enable upload of heartbeat record data from any device, including smartphone 110 or desktop PC 112, to the assessment server 104. The web interface may also enable the subject 106, via devices 110 and/or 112, to access their own data that has been stored and processed by the assessment server 104.

The system 100 also includes a knowledge base 124, which contains information generated via machine learning methodologies, using data obtained via expert evaluation of one or more training sets of subjects, and embodying a computational model of a relationship between mental state, i.e. subject stress levels, and heart rate characteristics.

Various machine-learning methodologies may be employed in different embodiments of the invention, including: decision tree learning; association rule learning; artificial neural networks; inductive logic programming; support vector machines; cluster analysis; Bayesian networks; reinforcement learning; representation learning; similarity learning; sparse dictionary learning; and/or genetic algorithms.

Embodiments described herein, particularly with reference to FIGS. 4 to 7, employ techniques including metric learning and clustering. However, these approaches should be regarded as illustrative only, and do not exclude the use of other learning techniques and computational models from the scope of the invention.

The knowledge base 124 may be contained within the non-volatile storage 116, or may be stored in a separate storage device, which may be directly connected to the assessment server 104, or may be remotely located. In particular, since the knowledge base 124 may ultimately grow to contain very large amounts of training and historical subject data, it may be advantageous for the knowledge base 124 to be stored in a large data centre and/or one or more distributed databases, e.g. in a cloud storage service. The exact form and location of the knowledge base 124 is not critical, so long as the required data, as described below, is accessible for processing by the assessment server 104.

Figure 2A:
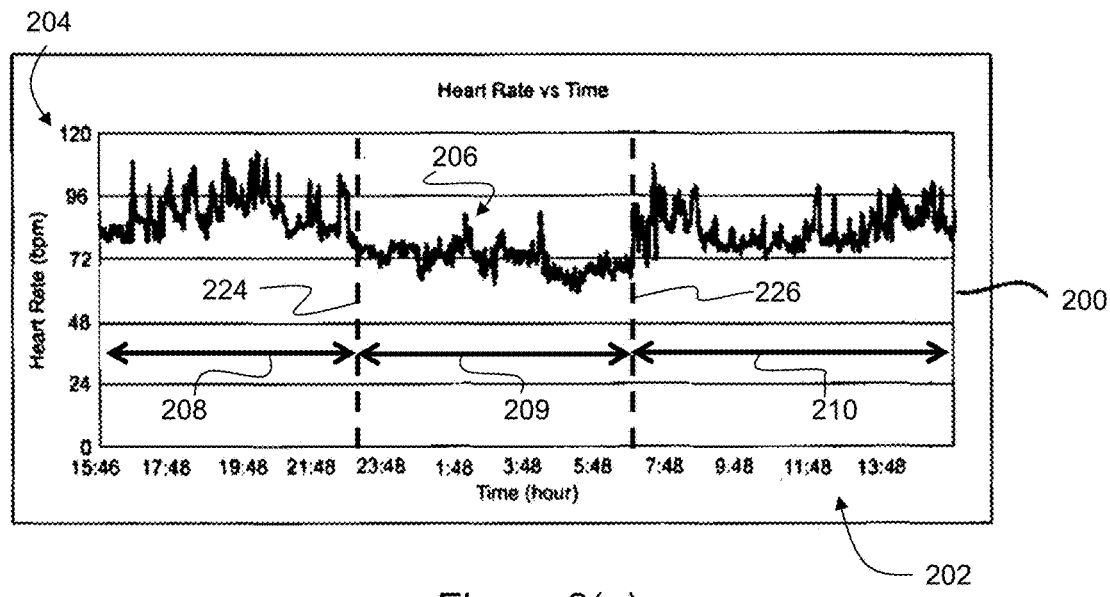
FIGS. 2(a) and 2(b) shows graphs of exemplary heart rate and activity records embodying the invention.

Turning now to FIG. 2(a), there is shown a graph 200 of an exemplary heartbeat record of a subject 106. Time is shown on the horizontal axis 202, and minute-averaged heart rate in beats per minute, on the vertical axis 204. Accordingly, the heartbeat record of the subject represented by the graph 200 comprises a sequence of heartbeat data samples, obtained and recorded at a rate of one per minute over the total timespan illustrated on the horizontal axis 202. In this particular example, the record covers a full 24-hour period, however embodiments of the invention may require only a portion of the full record 206, comprising a pre-sleep period 208, a sleep period 209, and a post-sleep period 210.

Figure 2B:
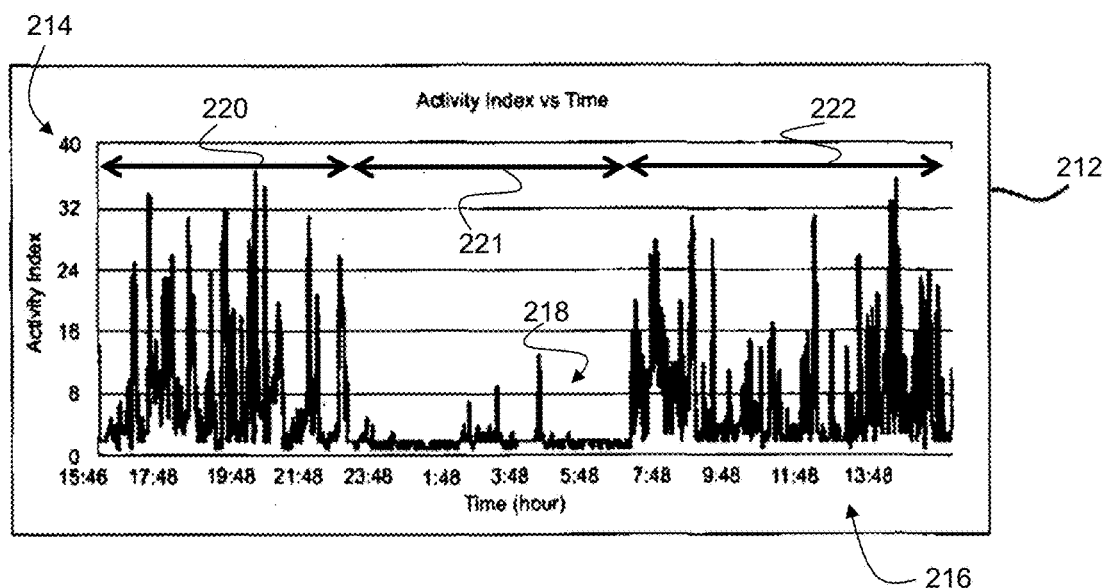

In some embodiments, the pre-sleep 208, sleep 209 and post-sleep 210 periods may be automatically identified. One technique for automatic identification of the sleep period 209 is through the use of an activity monitor, such as an accelerometer which may be incorporated into the heart rate monitor 108, or into another wearable device worn by the subject 106. FIG. 2(b) shows a graph 212 of subject activity obtained using such an activity monitor, and corresponding with the heartbeat record of FIG. 2(a). The horizontal axis 214 shows time, while the vertical axis 216 is an activity index, which is computed based upon the level of activity detected by the activity monitor during each minute of the recording period. The trace 218 of the activity record shows three very distinct periods, i.e. a first waking period 220 of relatively high activity, a sleep period 221 in which there is little or no activity, and a further waking period 222 of high activity.

The extremely distinct transitions between periods 220, 222, of high activity, and period 221 of low activity, enables relatively simple and accurate extraction of a sleep onset time 224 and a sleep conclusion time 226, separating the pre-sleep 208, sleep 209, and post-sleep 210 periods.

While activity levels provide one mechanism to identify the sleep onset 224 and sleep conclusion 226 times, other methods may be used in alternative embodiments. For example, it is also apparent from the graph 200 that the sleep period 209 corresponds with a general reduction in heart rate. Accordingly, suitable processing of the heartbeat record 206 may be employed to assist in identifying the sleep onset 224 and sleep conclusion 226 times. Additionally, or alternatively, the subject 106 may provide an estimate of sleep and waking times in order to assist in the detection of sleep onset 224 and conclusion 226. It will therefore be appreciated that various techniques to identify these transition times with sufficient accuracy and reliability are available for use in different embodiments of the invention.

Figure 3:
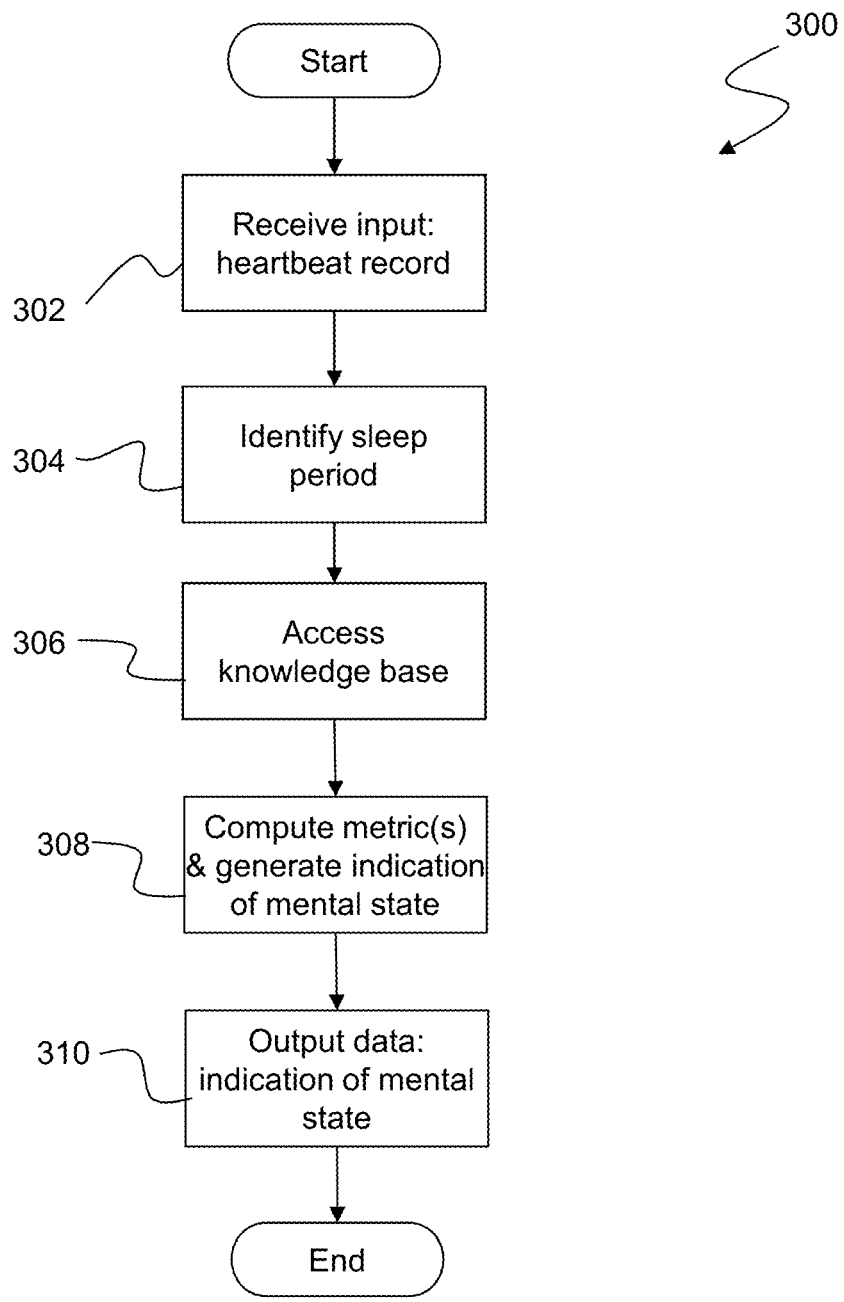
FIG. 3 shows a flowchart of a method of assessing a mental state embodying the invention.

FIG. 3 is a flowchart 300 showing a method of assessing a mental state, i.e. stress level, of the subject 106, according to an embodiment of the invention. Firstly, at step 302, a heartbeat record of the subject is received as input. In initial processing 304, the sleep period 209, having sleep onset time 224 and sleep conclusion time 226, is identified.

The assessment method 300, which may be implemented via suitable program instructions executed by the processor 114 of the assessment server 104, then proceeds to further analyse the heartbeat record in order to perform an assessment of the subject's stress levels. In order to do this, information in the knowledge base is accessed 306. Exemplary contents of the knowledge base are described below with reference to FIGS. 5(a) to 5(c), while corresponding exemplary training methods for constructing the knowledge base are described with reference to FIGS. 7(a) to 7(c). For present purposes it is sufficient to note that the information accessed in the knowledge base is based upon expert evaluation of a training set of subjects, and is constructed so as to enable the assessment server 104 to estimate the mental state of the subject 106 based upon the knowledge base contents. Generally, this involves a process 308 of computing one or more metrics associated with the mental state of the subject 106, and generating an indication of the mental state based upon those metrics.

At step 310 a resulting indication of mental state, i.e. stress level, is output. The output result may be stored in a subject record within the non-volatile storage 116, in the knowledge base 124, or in some other database. Alternatively, or additionally, the resulting indication may be presented to the subject, for example via a web interface, or via an application interface, using software executing on the subject device, such as the smartphone 110 or desktop PC 112.

Figures 4A, 4B, 4C:
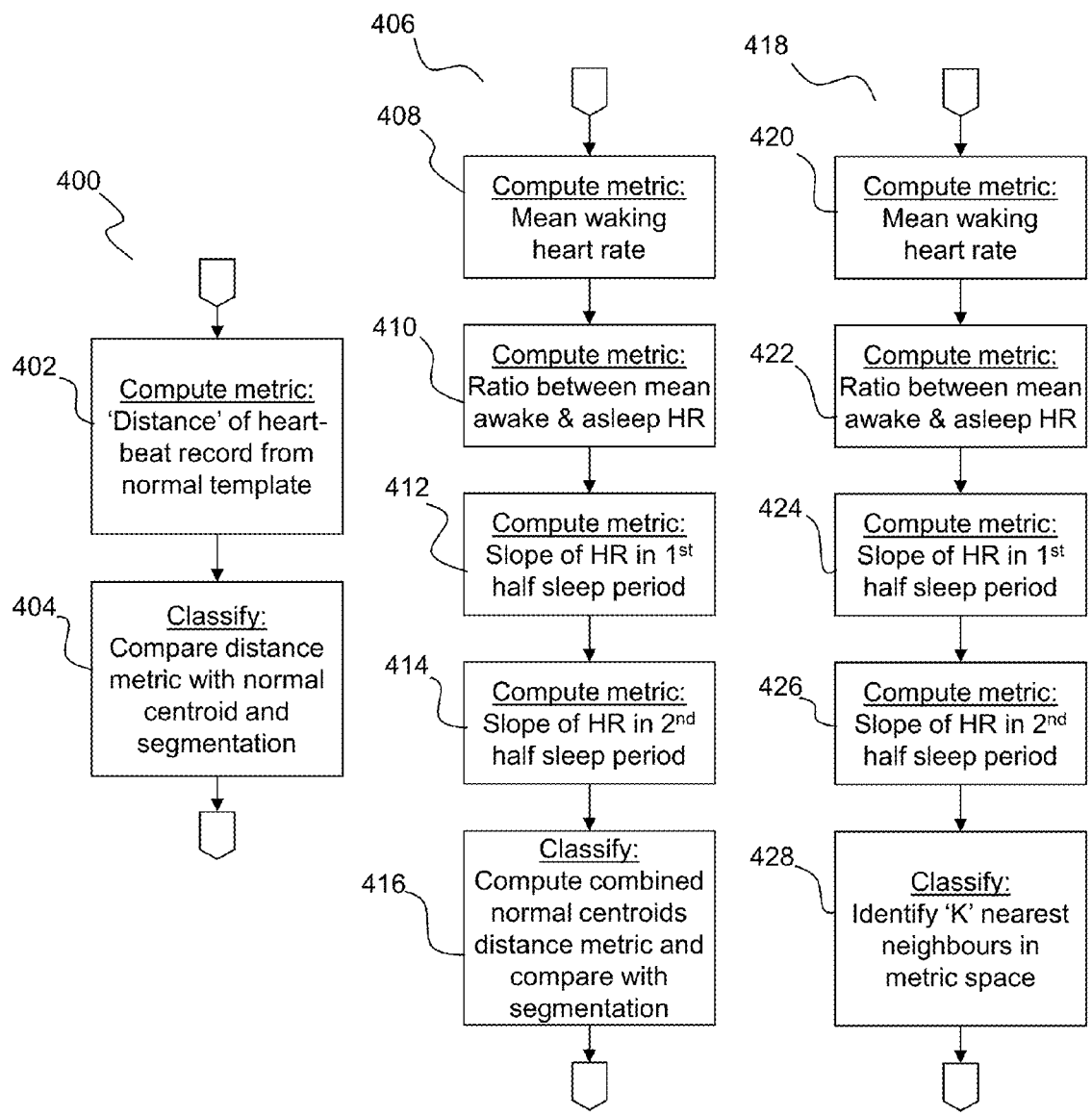
FIGS. 4(a) to 4(c) are flowcharts corresponding with three alternative computational models embodying the invention.
Figure 5A:
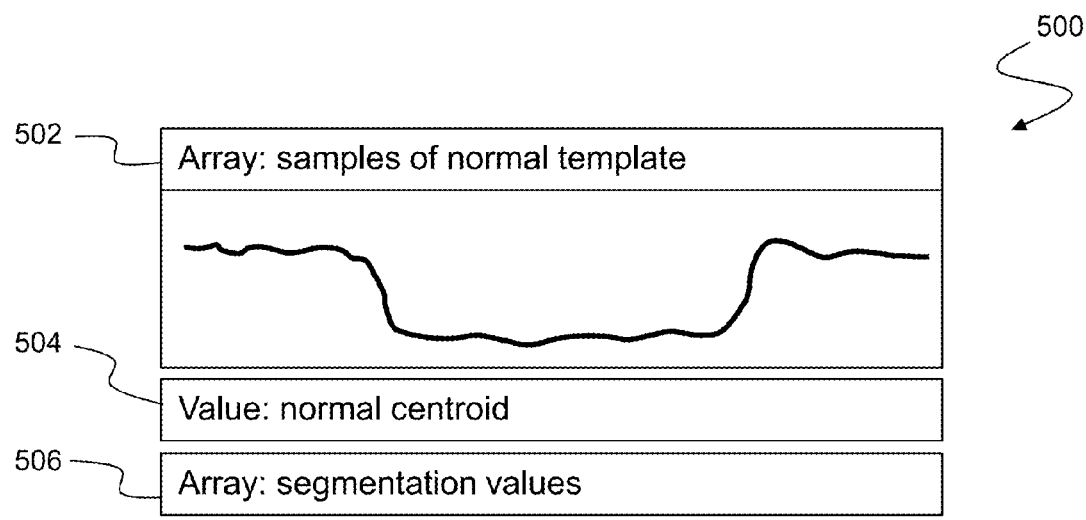
FIGS. 5(a) to 5(c) are block diagrams illustrating the content of knowledge bases corresponding with the computational models of FIGS. 4(a) to 4(c)
Figure 5B:
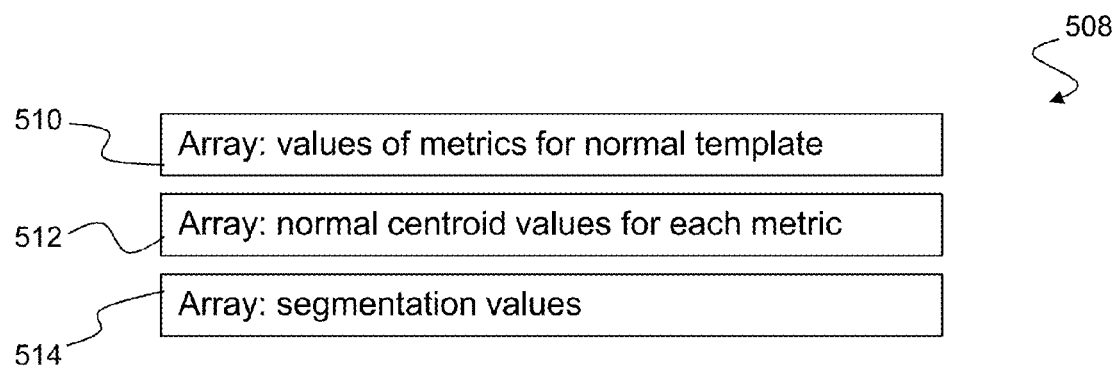
Figure 5C:
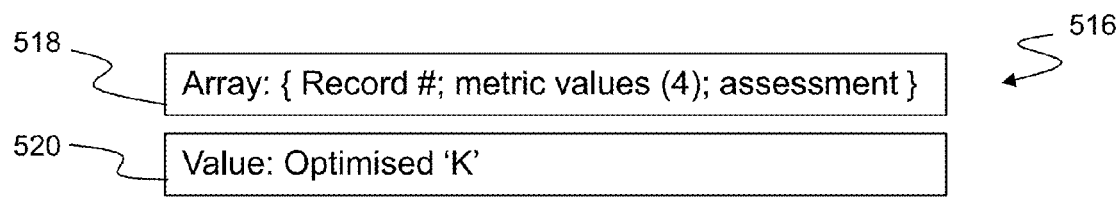

FIGS. 4(a) to 4(c) are flowcharts corresponding with three alternative computational models embodying the invention. FIGS. 5(a) to 5(c) are block diagrams illustrating the corresponding contents of the knowledge base for each of these models.

According to a first model, herein termed the 'template model', a process of computing a metric and generating an indication of subject stress level is represented by the flowchart 400, and the knowledge base contents 500. More particularly, the knowledge base 124 contains content 500 which includes a 'normal template' 502. The normal template 502 is a representative record corresponding with an unstressed, or only mildly stressed, subject. The way in which the normal template 502 is obtained will be described in greater detail below with reference to FIG. 7(a). The knowledge base content 500 also includes a value 504 termed the 'normal centroid'. The normal centroid 504 is a number representing a typical difference between the normal template 502 and an individual unstressed, or only mildly stressed, subject within the training set, as diagnosed by an expert assessor. Returning to FIG. 4(a), in step 402 a metric is computed for the assessment subject 106, which comprises a measure of difference between the heartbeat record of the subject, and the normal template 502. At step 404, a classification is performed by comparing the metric computed at 402 with the normal centroid 504. The magnitude of the difference is used to classify the subject 106 as one of: normal to mildly stressed; moderately stressed; or severely stressed. This classification is performed by comparing the magnitude of the difference with a set of segmentation values 506 also within the content 500 of the knowledge base 124.

The flowchart 406, and corresponding knowledge base content 508, illustrate a second computational model, termed the 'multi-parametric/distance model'. The multi-parametric models described herein employ four metrics that are computed from the input heart rate record of the subject 106. These four metrics are:

- the mean awake heart rate, i.e. the average heart rate during the pre-sleep 208 and post-sleep 210 periods;
- the ratio of heart rates, computed as a ratio between the average waking heart rate, and the average heart rate during the sleep period 209;
- a first slope metric, being a measure of the slope (i.e. change as a function of time) of the subject's heart rate during the first half of the sleep period 209; and
- a second slope metric, being a measure of the slope of the heart rate in the second half of the sleep period 209.

As will be appreciated, these four parameters fully define a piecewise-linear representation of the patient heartbeat record, having a constant waking heart rate value and a sleeping heart rate value that changes in accordance with the first slope metric during the first half of the sleep period 209, and in accordance with the second slope metric during the second half of the sleep period 209. The inventors have found this particular parameterisation of the heartbeat record to provide an effective basis for machine learning and prediction of stress levels, with the assistance of expert assessment of subjects in a training set.

Accordingly, at steps 408, 410, 412 and 414 the four metrics described above are computed. The content 508 of the knowledge base 124 includes an array 510 which comprises values of the four metrics corresponding with the normal template, i.e. average values from the normal to mildly stressed subjects in the training set. The knowledge base content 508 further includes an array 512 of corresponding normal centroid values for each metric, i.e. the representative difference between the average values in the array 510 and all of the actual individual subjects within the training set. At step 416, the metrics computed from the heartbeat record of the subject 106, at steps 408 to 414, are compared with the corresponding normal centroid values 512. The magnitudes of the differences are combined to compute a single 'distance' value, which is then compared with a set of segmentation values 514 within the knowledge base content 508. These segmentation values classify the state of the subject 106 into normal to mildly stressed, moderately stressed, or severely stressed.

A method of classifying the stress level of the subject 106 according to a third computational model is shown in the flowchart 418. This method is again based on the four metrics described above, which are computed at steps 420, 422, 424 and 426 respectively. At step 428, a classification is performed according to a k nearest neighbour (k-NN) computational model. Accordingly, this model is termed the 'multi-parametric/k-NN model'.

The content 516 of the knowledge base 124 for the multi-parametric/k-NN model is illustrated in FIG. 5(*c*). The content 516 comprises an (M+2) dimensional array 518. The array 518 contains, for each subject in a training set, an (M+1) dimensional vector, where M is the number of metrics within the multi-parametric model, i.e. M=4 in the current example. Each vector contains, for an individual training set subject, the computed values of the M metrics, along with the corresponding assessment rating as determined by the expert assessor. The values of the metrics may be regarded as defining a point in an M-dimensional metric space, while the expert rating provides a value associated with the point.

The knowledge base content 516 also includes a value 520 which is an integer defining an optimised value K. The classification step 428 in the process 418 comprises finding the K nearest neighbours from the array 518 to the point in the metric space defined by the four metrics computed at steps 420 to 426. The values of the expert ratings associated with these K nearest neighbours are used to classify the stress level of the subject 106. In one embodiment, a majority voting algorithm is employed, whereby the subject's stress level is classified according to the most frequent expert rating of the K nearest neighbours. Accordingly, the k-NN algorithm effectively operates on the basis of clusters of similar expert assessments existing within the M dimensional metric space.

Turning now to FIG. 6, there is shown a block diagram 600 illustrating the main software processing components of a computer implementation embodying the invention. The input heartbeat record data 602 is processed by sleep detection module 604, in order to identify the sleep onset and conclusion times. The record is optionally further processed by a rescaling module 606. The rescaling module processes the input data 602 in order to obtain a rescaled record, wherein the heart rate values have been normalised between zero and one, and the time adjusted to a standard scale, e.g. zero to 1,000 time units. Of the embodiments described in detail above, the rescaling is required only for the template model, in which it is important to ensure similarity among all of the heartbeat records that are being compared against the normal template 502. Rescaling is not required for the multi-parametric models described above, although it may be used in the computation of other metrics in accordance with alternative embodiments of the invention.

Metric calculation module 608 computes the relevant metric, or metrics, associated with the particular computational model used in an embodiment of the invention. For example, in the template model the metric calculation module 608 computes a value representing the difference between the heartbeat record of the subject 106 and the normal template 502. In the multi-parametric models, the metric calculation module 608 computes the four metrics described above, with reference to FIG. 4(*b*).

In some embodiments, in order to compute the metric, or metrics, the metric calculation module 608 accesses the knowledge base 124. For example, in the template model, the metric calculation module 608 retrieves the normal template 502 from the knowledge base 124.

The decision module 610 classifies the stress level of the subject 106 according to the rules associated with the particular computational model. For example, in the template model, and the multi-parametric/distance model, the decision module 610 classifies the stress level of the subject 106 by comparing a computed distance metric with the segmentation values 506, 514.

In the multi-parametric/k-NN model, the decision module 610 classifies the stress level of the subject 106 according to the most frequent expert assessment rating of the K nearest neighbours.

Typically, the decision module 610 requires access to the knowledge base 124, in order to retrieve the decision criteria. An output stress level indication 612 is produced from the decision module 610.

Figure 7C:
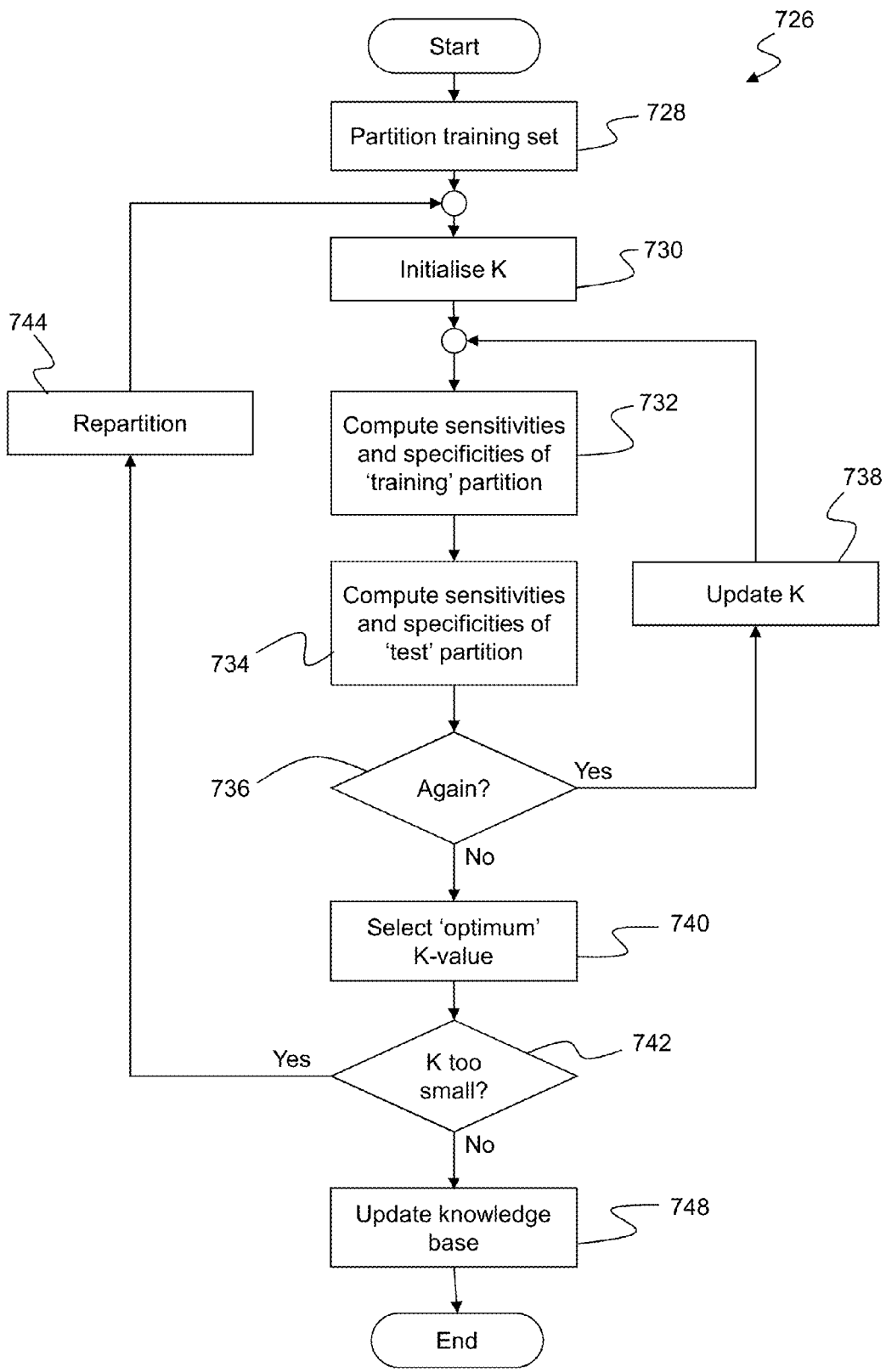
Figure 7D:
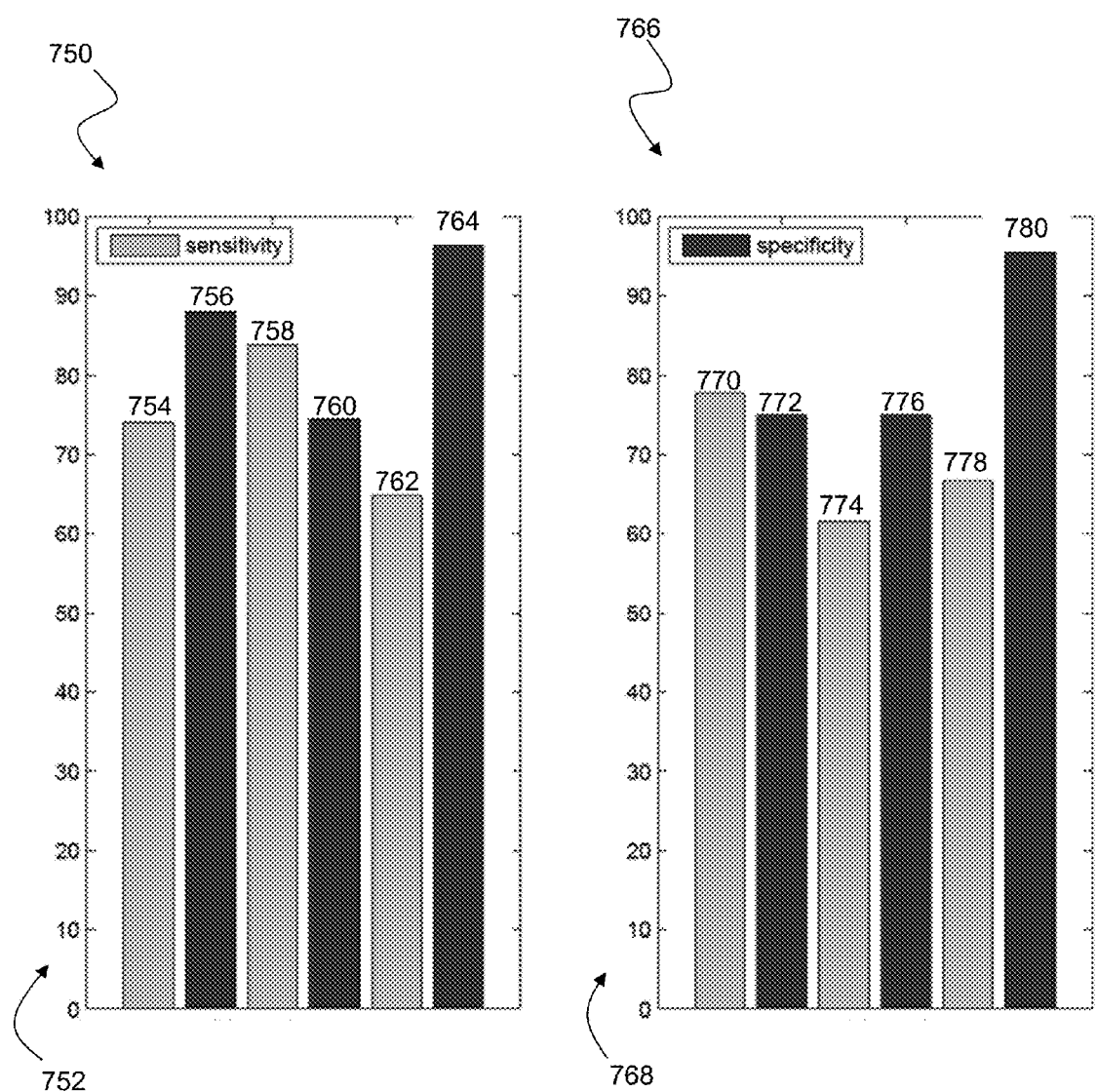
FIG. 7(d) illustrates exemplary performance of a computerised model embodying the invention.

FIG. 7(*a*) shows a flowchart 700 corresponding with the algorithm for knowledge base construction according to the template model. For this algorithm, and for the other two algorithms discussed below with reference to FIGS. 7(b) and 7(c), a precondition is that the knowledge base 124 includes a data set of training records. Each training record comprises a heartbeat record of a test subject, along with an associated diagnosis/assessment performed by an expert, such as a trained medical practitioner. The assessment may be conducted based upon the expert's review of the test subject heart rate records or may be obtained by other diagnostic means, such as interviews between each test subject and the expert assessor. It is these actual assessments associated with the data in the training set that provide the primary expert knowledge within the knowledge base. This information is then used to build computational models embodying this expert knowledge, which can then be used to predict the mental state, i.e. the stress level, of a subsequent unseen subject 106, based upon an input heartbeat record of the subject.

Returning to the template model training algorithm 700, at step 702 all test subject data associated with an assessment of 'normal to mild' stress level are retrieved from the knowledge base 124. Each record comprises a sequence of heartbeat data samples, such as those illustrated in the graph of FIG. 2(a). As has already been described, at step 708 the retrieved normal data records are rescaled, such that heart rate is normalised between zero and one, and sleep period durations are normalised to a common timescale.

At step 706 an average of all of the retrieved and rescaled test subject records is computed. This is a sample-by-sample averaging process, which results in the generation of a single representative heartbeat record, known as the 'normal template'.

At step 708, for each one of the retrieved normal test subject records, a measure of distance from the normal template is computed. Any suitable distance measure may be used, and in exemplary embodiments a least-squares distance measure is employed.

At step 710, an average of all the distance measures is computed. This average value is termed the 'normal centroid'.

The template model assumes that a single distance measure, and more particularly a difference between the normal centroid and the equivalent distance measure for a subsequent heartbeat record of a subject 106, may be used to classify the stress level of the subject. Accordingly, a set of segmentation values is required defining the boundaries between normal to mild stress, moderate stress, and severe stress levels. For this three-level classification, two segmentation values are required, and are computed at step 712.

The present inventors have found that clear boundaries do not exist between different proposed stress level classifications, and that there is some 'intermingling'. However, generally speaking it has been found that the greater the distance between a computed distance measure for a particular subject 106, and the normal centroid, the more-highly stressed the subject is likely to be. Accordingly, appropriate statistical techniques must be used in order to define the segmentation values forming the boundaries between stress levels. In some embodiments, Gaussian mixture models (GMM) are used for this purpose.

The flowchart 714 in FIG. 7(b) illustrates the knowledge base construction algorithm for the multi-parametric/distance model. As with the template model algorithm 700, the algorithm 714 commences by retrieving all records for normal to mild subjects from the training set, at step 716. The four metrics are computed for all of the retrieved records, and corresponding average values of the metrics computed at step 718.

At step 720, for each of the retrieved normal to mild data records, a measure of the distance between the individual metrics and the corresponding averages is computed. All of these individual distance measures are then averaged to produce a vector of four 'normal centroids', corresponding with each one of the four metrics, at step 722.

In the multi-parametric/distance model, differences between the individual values of metrics computed for the heartbeat record of the subject 106, and the corresponding normal centroid values, are computed and then combined to form a single distance measure. This distance measure may be a simple sum of the magnitudes of individual differences, a weighted sum, a Euclidian distance, or any other suitable distance measure. Having reduced the difference data to a single distance measure, a set of segmentation values defining the boundaries between stress levels may then be determined, as for the template model. This determination of segmentation values is performed at step 724. Again, one practical approach is to employ a Gaussian mixture model using all of the data in the training data set, i.e. computing the distance measures associated with all of the moderate and severely stressed subjects within the training set, as well as the subjects having normal to mild stress levels.

The flowchart 726 in FIG. 7(c) illustrates the knowledge base construction algorithm for the multi-parametric/k-NN model. The algorithm 726 commences, at step 728, by dividing the training set into training and test partitions. For example, 90 percent of the subject records in the training set may be used for training, and 10 percent for testing the effectiveness of the training against the known expert assessments. The effectiveness of the resulting computational model may be dependent upon the size of the training and test partitions, as well as the particular composition of test subject records making up each partition. Accordingly, different techniques may be employed in order to partition the training set, including random selection of members for the training and test partitions, and/or selection of specific records as members of the training and/or test partition. As described further below, the algorithm 726 may employ repartitioning of the training set in an effort to optimise the effectiveness of the computational model.

At step 730, an initial value of K (i.e. the number of nearest neighbours employed in the k-NN calculation) is selected. Any positive integer may be chosen, however it is generally not productive to set K=1. This is because, when K=1, each record in the training partition determines only its own predicted assessment of mental state, which is therefore guaranteed to be correct. A perfect result will therefore be achieved for the training partition, without providing any control over the quality of predictions for unseen data, such as records in the test partition.

The quality measures used in the exemplary embodiment for assessing results based on the training and test partitions are sensitivity and specificity. Sensitivity is defined as the proportion of correct classifications of a particular rating, e.g. the proportion of all subjects assessed by the expert to be moderately stressed who are correctly identified as being moderately stressed by the computational model. Specificity is defined as the proportion of all subjects assessed by the expert not to fall within a particular classification (e.g. moderately stressed) who are incorrectly classified by the computational model within that particular classification.

Accordingly, at step 732 sensitivities and specificities are computed for all of the records within the training partition, for the current value of K. It should be noted that, while all of the actual mental states associated with the records in the training partition are assumed to be known, a particular member of the set may be 'outvoted' by its nearest neighbours. The results of computing the sensitivities and specificities for the training partition, and in particular a reduction of sensitivities below 100 percent, is thus a measure of how well clustered the selected members of the training partition are within distinct regions of the metric space. Of particular interest are 'outliers', i.e. individual data points having an associated assessment of mental state that is different from all, or a majority, of nearest neighbours within an associated volume of the metric space.

At step 734, sensitivities and specificities are computed for the test partition. Mental states associated with records within the test partition are assumed not to be known, and are predicted according to the K nearest neighbour classification rule. The predictions are then compared with the actual expert assessments, in order to obtain the sensitivities and specificities for the test partition.

A decision is made, at 736, whether to repeat steps 732 and 734 of computing the sensitivities and specificities for a further, different, value of K. If this is desired, the value of K is updated at step 738, and steps 732 and 734 are repeated. For example, the process may sweep through a range of values of K, or may use a maximisation procedure to adjust K in order to converge upon a value that maximises a measure of quality of the predictions made by the computational model.

In particular, one measure of quality is the average of the sensitivities and specificities across all of the classifications of mental state, e.g. normal to mild stress, moderate stress and severe stress. By maximising such a measure across the training and test partitions a value of K may be selected for which the predictions of the model, for future unseen data records, will be optimum in a corresponding sense. Accordingly, at step 740 a value of K is selected in this manner. The result is a model comprising the selected training partition, along with the selected value of K, which is used in the k-NN algorithm for prediction of mental state associated with unseen heartbeat records.

A further observation regarding the k-NN algorithm is that, for a given quality of the model (e.g. measured in the manner described above) a larger value of K generally corresponds with a more-stable and accurate model than a small value of K. This is because larger values of K correspond with larger numbers of nearest neighbours being used to determine the predicted classification of an unseen record. On the other hand, a good quality model will not be obtained for excessively large values of K, because this significantly reduces the specificity.

Overall, however, it may be desirable to run the algorithm with a number of different partitions of the training set, in order to identify a training partition that produces high sensitivity/specificity on average, in combination with a relatively larger value of K. Accordingly, at step 742, if the value of K is considered too small, the training set may be repartitioned at step 744, and a new optimisation for K conducted using the new partitions, by repeating steps 730 to 740. The repartitioning at step 744 may be random, or it may be deterministic. For example, a deterministic repartitioning may involve identifying outliers within the training set, and selectively removing or moving them to the test partition. Furthermore, a combination of deterministic and random partitioning may be employed. For example, the training set may first be partitioned into records corresponding with each of the mental states (i.e. normal to mild stress, moderate stress and severe stress), and then randomly partitioning each of these subsets into the training and test partitions in equivalent proportions, to ensure that all of the stress levels are proportionately represented in both partitions. Furthermore, suitable optimisation techniques may be employed in order to create an improved training partition upon repartitioning. For example, simulated annealing, or some other approximate optimisation technique, may be used in generating successive partitions in an effort to maximise the quality of classification over the available training set.

Once a final training partition and value of K have been selected, at step 748 the knowledge base is updated with these values. By way of illustration, FIG. 7(*d*) shows bar charts of exemplary sensitivity and specificity values resulting from execution of the algorithm 726 over a particular training set. In this case, 90 percent of records in the overall training set were included in the training partition, and the remaining 10 percent in the test partition. This same proportion was employed for all three stress classifications. For this example, K=6, and outliers were distributed across both the training and test partitions. As a result, consistently high average sensitivities and specificities have been achieved across all three classifications within both the training and test partitions.

The left-hand bar chart 750 shows sensitivity and specificity for the training partition, where the vertical axis 752 represents a percentage. The bar chart shows sensitivity 754 and specificity 756 for normal to mild stress, sensitivity 758 and specificity 760 for moderate stress, and sensitivity 762 and specificity 764 for severe stress. The bar chart 766 on the right shows the results for the test partition, with the vertical axis 768 again being percentage. This chart shows sensitivity 770 and specificity 772 for normal to mild stress, sensitivity 774 and specificity 776 for moderate stress, and sensitivity 778 and specificity 780 for severe stress.

Notably, in both bar charts 750, 766 the highest value achieved is for specificity 764, 780 of severe stress assessments in both partitions. This implies that the computational model very rarely misclassifies severe cases. Consequently, the computational model is more likely to misclassify normal to mild stress as moderate, and/or vice versa. It is reasonable to assume, given these results, that misclassification becomes less likely in more highly stressed subjects. This is a desirable property of the computational model, when it is used for self-assessment and/or in conjunction with assessment and treatment by a health care professional. That is, the model may be used to enable individuals to monitor and manage their own stress levels, and/or to encourage them to seek professional assistance and support when stress levels become excessive for extended periods of time.

With this in mind, it is desirable to make the stress assessment available to individuals, for example via the system 100 illustrated in FIG. 1. The assessment server 104 implements a computational model, such as those described above. An assessment subject 106 can access the assessment server 104 via a smartphone 110 running a suitable application, and/or via a web interface on a smartphone 110 or PC 112. Access using a smartphone 110 may be advantageous, because a smartphone app may be developed that is able to communicate with a heart rate monitor device, gather data over a measurement period, and transmit the resulting heartbeat data record to the assessment server 104.

Figure 8:
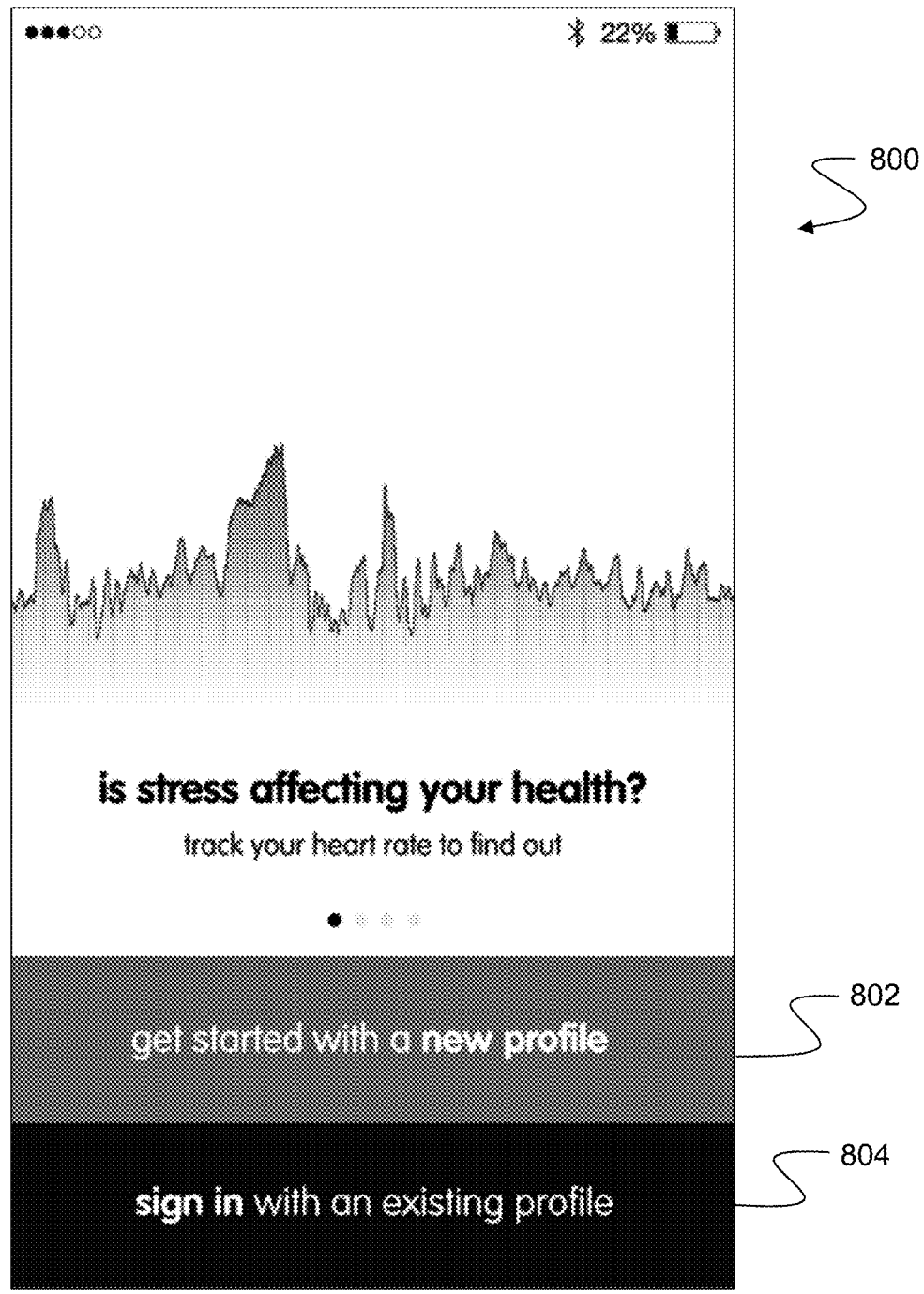
FIGS. 8 to 12 show exemplary screen displays of a smartphone application embodying the invention.

FIG. 8 therefore shows an exemplary screen display of a suitable smartphone application embodying the invention. The display 800 provides an introduction to the application, and provides touchscreen buttons 802, 804 to enable the user to register with the assessment server 104 (i.e. 'get started with a new profile'), or to log into the assessment server 104 (i.e. 'sign in with an existing profile').

Figure 9:
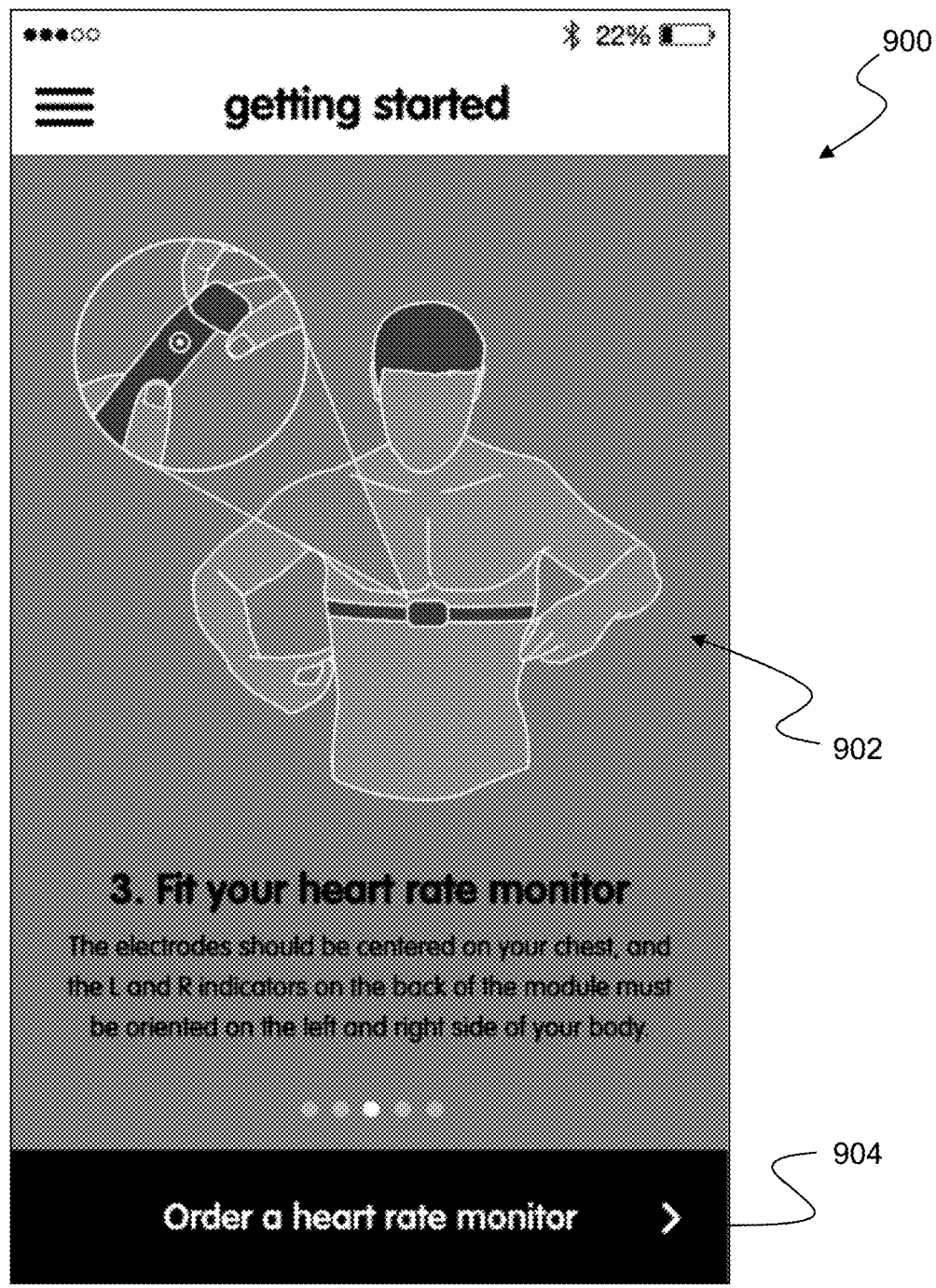

FIG. 9 shows a further exemplary smartphone application display 900, which contains instructions 902 for the user 106 to fit their heart rate monitor device 108. If the user does not have a suitable heart rate monitor device, a touchscreen button 904 is provided which enables a heart rate monitor device to be ordered, e.g. via an order form (not shown) implemented by the assessment server 104, or by a further e-commerce server (not shown in the drawings) connected to the Internet 102.

Figure 10:
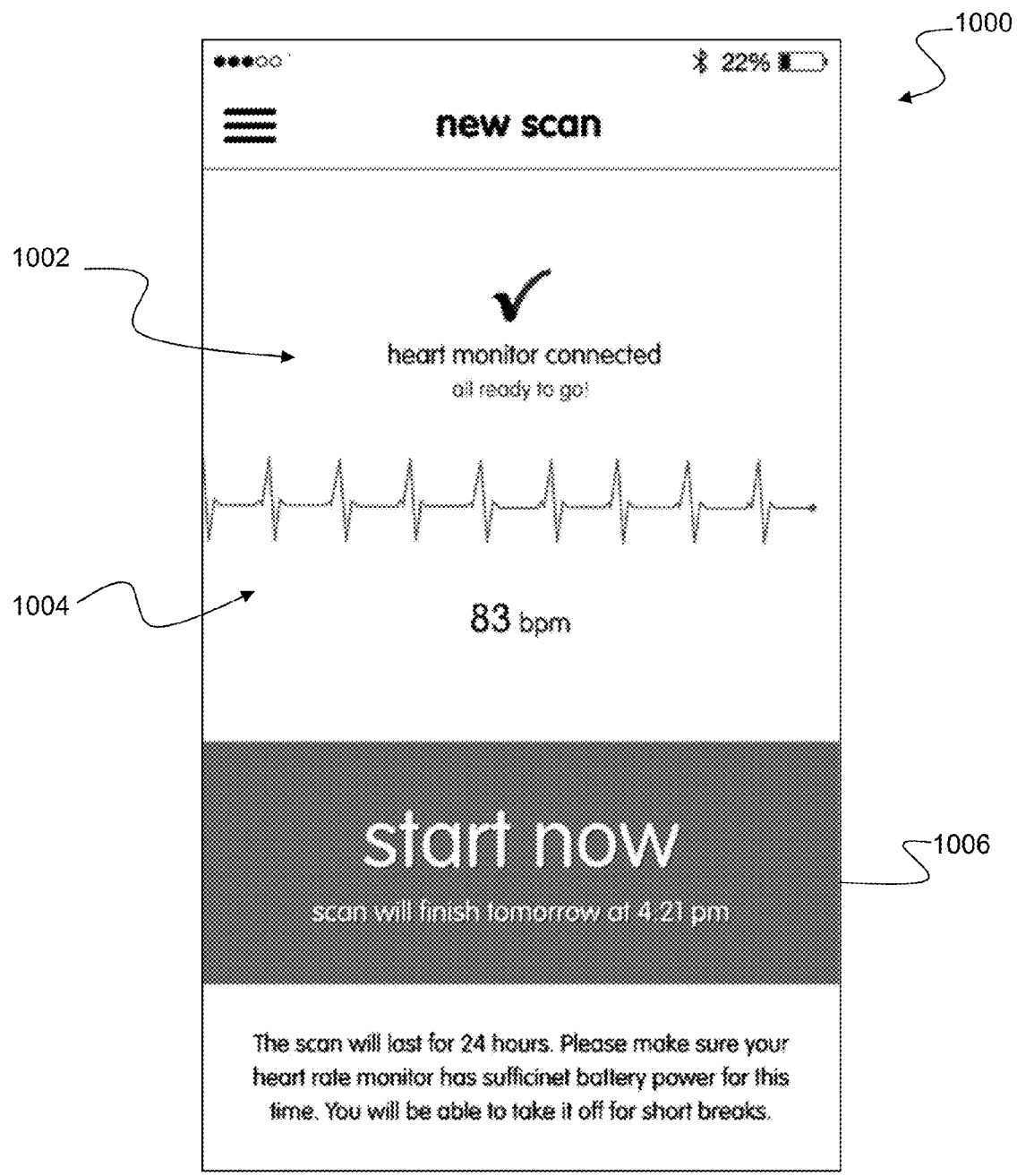

FIG. 10 shows a further exemplary display 1000 of the smartphone application, which includes an indication 1002 that the heart rate monitor device 108 has been successfully contacted, e.g. via Bluetooth or other wireless connection, and a representation 1004 of a current heart rate as measured by the monitor device. Once a connection to the heart rate monitor device 108 has been established, the user can touch the button 1006 to commence measurement of a heartbeat record, comprising a sequence of heartbeat data samples obtained over a timespan including a sleep period. The timespan may comprise a full 24 hours, or may comprise a shorter period including sufficient pre-sleep and post-sleep periods to enable the onset and conclusion of sleep to be identified, and waking heart rate data to be analysed, as required in the algorithms described above.

Figure 11:
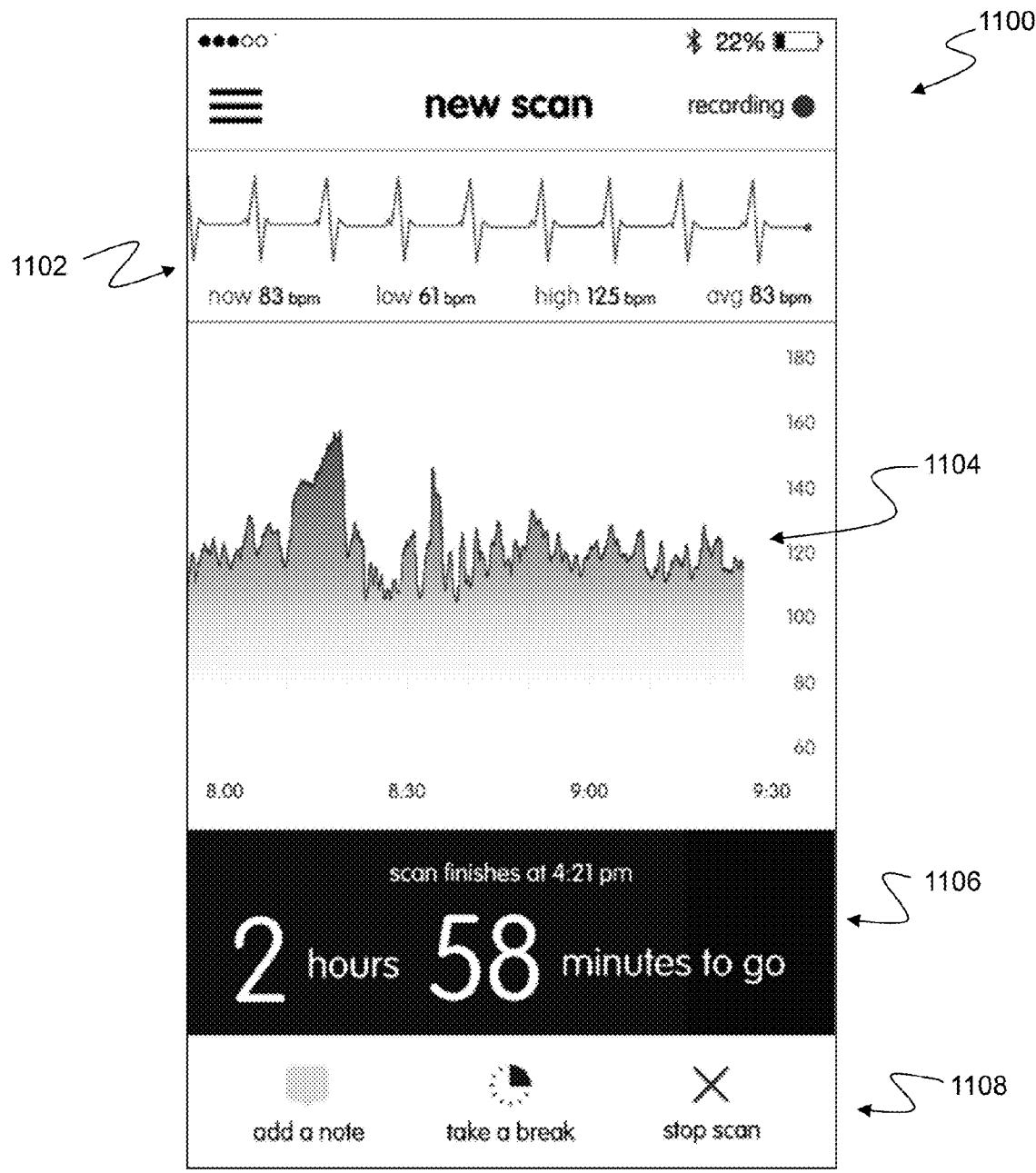

FIG. 11 shows a further exemplary application display 1100 that may be provided to the user 106 during the course of a measurement. An upper region 1102 of the display provides a summary of key data, including current heart rate, minimum and maximum heart rate, and average heart rate, over the course of the current measurement. A central region 1104 of the display shows a graph of the minute-averaged heart rate over the entire course of the current measurement. The remaining measurement time is shown in the panel 1106. Finally, additional touch-screen controls are provided in a lower region 1108 of the display, enabling the user 106 to add a note, and to pause or stop the measurement.

Figure 12:
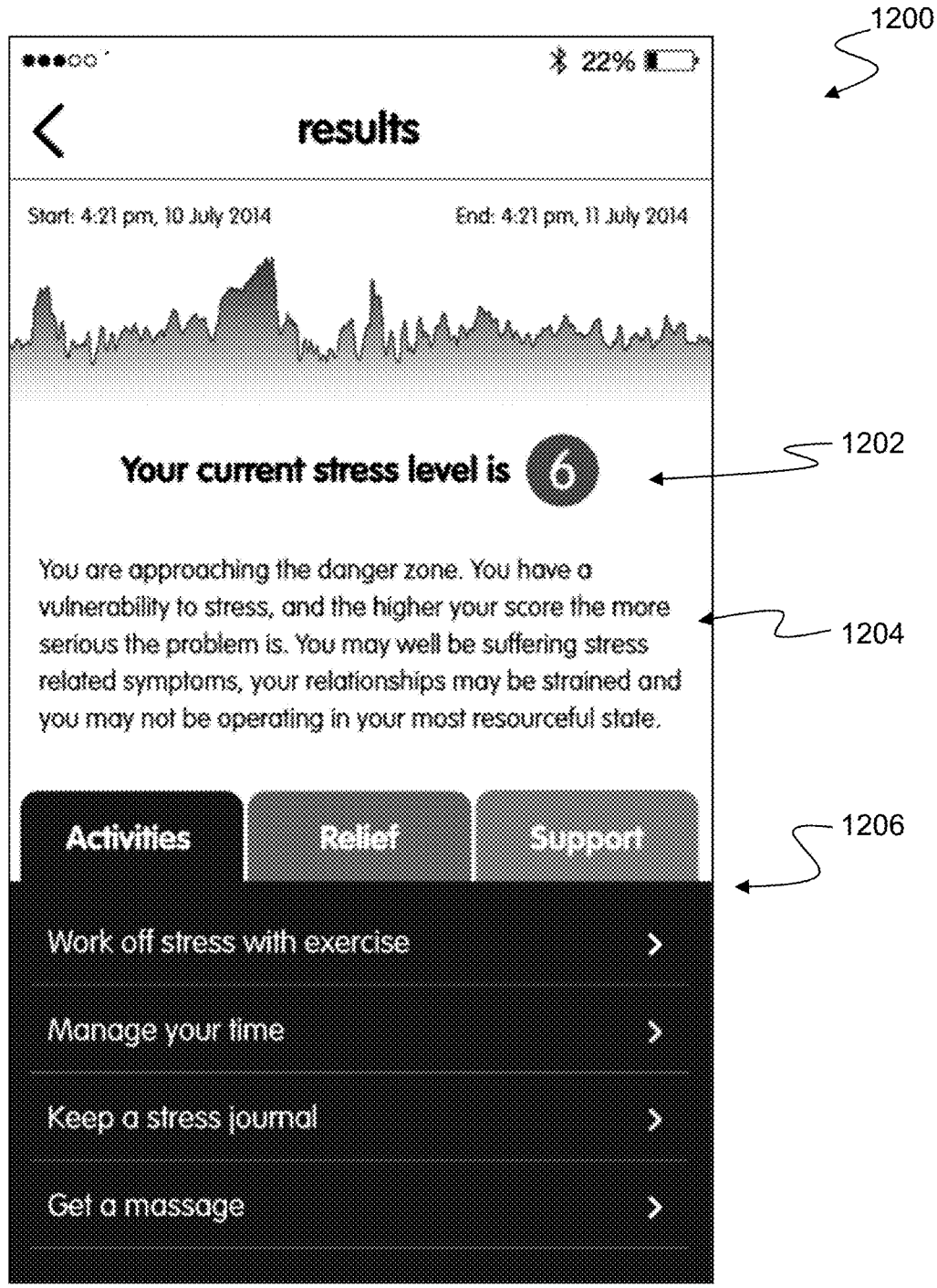

FIG. 12 shows a display 1200 that may be provided to the user 106 upon completion of the measurement, and analysis of the results by the assessment server 104. The display 1200 includes an indication 1202 of stress level over the measurement period, as well as a plain-language interpretation of the result and the likely impact of this stress level on the subject 106. Finally, the application provides a tabbed region 1206 of the display, giving the user 106 easy access to various resources that may be of assistance in managing their stress levels.

In summary, embodiments of the present invention provide methods and systems enabling measurement, monitoring and assessment of mental state, and in particular stress levels experienced by individual subjects, via simple and non-invasive heartbeat measurements. An online service may be provided such that individuals are able to perform measurements at home, and while going about their normal daily activities. Assessments are automatically generated using computational models, for example executed on a server accessible via the Internet, using a knowledge base comprising expert assessment information.

Services and applications provided in accordance with embodiments of the invention may be available to subjects individually, or to their employers in order to monitor the psychological health of their employees. In particular, individuals and/or employees are enabled to check their stress levels, and to receive early warnings of being at risk of excessive or extensive stress. Furthermore, the assessment server 104, e.g. via a smartphone application or a web interface, may be used as a channel to provide educational material and further support to individuals based upon their assessed stress levels. The support may include recommending a visit to a general practitioner or other health professional. The assessment server 104 may keep historical records, and make these available via the Internet, such that individuals can conduct ongoing monitoring of stress levels, and check their progress.

Potential benefits of embodiments of the invention include improved analysis of stress levels associated with particular job classes and types, increased productivity due to reduced absenteeism and presenteeism, and reduced claims and reduced claims and pressure on the health care system. Accordingly, numerous benefits may be obtained by individuals, employers, and by society.

While particular embodiments have been described, by way of example only, a person skilled in the relevant arts will appreciate that a number of variations are possible, within the scope of the present invention. Accordingly, the exemplary embodiments should not be regarded as limiting, but rather the invention is as defined in the claims appended hereto.

The claims defining the invention are as follows:

1. A computer-implemented method of assessing a mental state of a subject, the method comprising:
receiving, as input, a heartbeat record of the subject, which comprises a sequence of heartbeat data samples obtained over a time span which includes a pre-sleep period, a sleep period having a sleep onset time and a sleep conclusion time, and a post-sleep period; identifying, within the heartbeat record, at least the sleep onset time and the sleep conclusion time;
accessing a knowledge base comprising data obtained via expert evaluation of a training set of subjects and embodying a computational model of a relationship between mental state and heart rate characteristics;
using information in the knowledge base, applying the computational model to a computed at least one metric associated with the mental state of the subject, to generate an indication of mental state based upon the metric, wherein the knowledge base comprises a template heart rate characteristic obtained by averaging scaled and normalised heart rate characteristics of subjects in the training set who have been assessed by an expert assessor as experiencing normal or low levels of stress; and
providing, as output, the indication of mental state.

2. The method of claim 1 wherein the indication of mental state comprises an indication of stress levels experienced by the subject.

3. The method of claim 2 wherein the indication of mental state distinguishes between three levels of stress.

4. The method of claim 1 wherein the knowledge base further comprises a normal centroid value, comprising a measure of an average distance of the heartbeat characteristics of subjects in the training set assessed as normal from the template characteristic.

5. The method of claim 4 wherein the knowledge base further comprises a set of segmentation points, representing variations in distance from the template characteristic, relative to the normal centroid and, defining classification boundaries between different indications of mental state.

6. The method of claim 2 wherein heart rate characteristics of subjects are processed to compute a plurality of associated metrics.

7. The method of claim 6 wherein the metrics comprise: a mean-awake heart rate; a ratio between mean-awake and -asleep heart rates; a slope of heart rate during the first half of the sleep period; and a slope of heart rate in the second half of the sleep period.

8. The method of claim 6 wherein the knowledge base comprises an array of values of the metrics corresponding with a template characteristic based upon subjects assessed by an expert as having normal or low stress levels.

9. The method of claim 8 wherein the knowledge base further comprises an array of normal centroid values, corresponding with each one of the plurality of metrics, and computed by averaging the magnitudes of the differences between the respective metrics for all subjects assessed by the expert as having normal or low stress levels, and the equivalent template characteristic metrics.

10. The method of claim 9 further comprising performing a comparison between the computed metrics for the received heartbeat record of the subject, and the corresponding normal centroid values, to compute a measure of distance of the subject's mental state from a 'normal' mental state, and wherein the knowledge base further comprises an array of segmentation values defining distance measures corresponding with boundaries between mental state classifications.

11. The method of claim 6 wherein the knowledge base comprises an array of (M+1) dimensional vectors, where M is the number of the plurality of metrics employed, in which each vector corresponds with a subject in the training set, and comprises values for each of the computed metrics, and a value of the corresponding expert assessment of the subject.

12. The method of claim 11 wherein the indication of mental state is generated using a k nearest neighbour (k-NN) computational model.

13. The method of claim 12 wherein the knowledge base further comprises an optimised value of the number of nearest-neighbours parameter K.

14. The method of claim 12 wherein the indication of mental state of the subject is generated as the most-frequently occurring mental state associated with the identified K nearest neighbours from the training set.

15. A computer-implemented system for assessing a mental state of a subject, the system comprising:
   at least one microprocessor;
   at least one non-volatile storage device containing a knowledge base comprising data obtained via expert evaluation of a training set of subjects and embodying a computational model of a relationship between mental state and heart rate characteristics;
   at least one computer-readable memory device operatively associated with the microprocessor; and
   an input/output interface operatively associated with the microprocessor, wherein the memory device contains computer-executable instruction code which, when executed via the microprocessor, causes the microprocessor to effect a method comprising steps of:
   receiving, via the input/output interface, a heartbeat record of the subject, which comprises a sequence of heartbeat data samples obtained over a timespan which includes a pre-sleep period, a sleep period having a sleep onset time and a sleep conclusion time, and a post-sleep period;
   identifying, within the heartbeat record, at least the sleep onset time and the sleep conclusion time;
   using information in the knowledge base, applying the computational model to a computed at least one metric associated with the mental state of the subject to generate an indication of mental state based upon the metric, wherein the knowledge base comprises a template heart rate characteristic obtained by averaging scaled and normalised heart rate characteristics of subjects in the training set who have been assessed by an expert assessor as experiencing normal or low levels of stress; and
   providing, via the input/output interface, the indication of the mental state of the subject.

16. The system of claim 15 wherein the heartbeat record of the subject is obtained via a heart rate monitor device worn by the subject during the timespan including the pre-sleep period, the sleep period and the post-sleep period.

17. The system of claim 16 wherein the heartbeat monitor comprises a communications interface configured for communication with a networkconnected device of the subject.

18. The system of claim 17 wherein the input/output interface comprises a network interface providing access to a wide area network, and the next record is received via the wide area network from the network-connected device of the subject.

* * * * *